United States Patent
Imai

(10) Patent No.: US 12,290,400 B2
(45) Date of Patent: May 6, 2025

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Yoshiro Imai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/156,498

(22) Filed: Jan. 22, 2021

(65) Prior Publication Data
US 2021/0137492 A1  May 13, 2021

Related U.S. Application Data

(63) Continuation of application No. PCT/JP2019/025851, filed on Jun. 28, 2019.

(30) Foreign Application Priority Data

Aug. 27, 2018 (JP) .................................. 2018-158208

(51) Int. Cl.
  *A61B 8/00*  (2006.01)
  *A61B 5/00*  (2006.01)
  *A61B 8/08*  (2006.01)

(52) U.S. Cl.
  CPC ............ *A61B 8/4254* (2013.01); *A61B 5/489* (2013.01); *A61B 8/0891* (2013.01); *A61B 8/461* (2013.01);
  (Continued)

(58) Field of Classification Search
  CPC ..... A61B 8/4254; A61B 8/0891; A61B 8/461; A61B 8/488; A61B 8/5207; A61B 8/54;
  (Continued)

(56) References Cited

U.S. PATENT DOCUMENTS 6,245,018 B1    6/2001 Lee
2008/0188752 A1*  8/2008 Randall ................. A61B 8/463
                                                 600/455
(Continued)

FOREIGN PATENT DOCUMENTS

JP    2008272025 A    11/2008
JP    2015167795 A     9/2015
(Continued)

OTHER PUBLICATIONS

The extended European search report issued by the European Patent Office on Sep. 23, 2021, which corresponds to European Patent Application No. 19856254.8-1126 and is related to U.S. Appl. No. 17/156,498.
(Continued)

*Primary Examiner* — Dixomara Vargas
(74) *Attorney, Agent, or Firm* — Studebaker Brackett PLLC

(57) ABSTRACT

An ultrasound diagnostic apparatus (1) includes an ultrasound probe (19), an image acquisition unit (8) that transmits an ultrasound beam toward a subject from the ultrasound probe (19) to sequentially acquire ultrasound images, a blood vessel detection unit (10) that detects a blood vessel included in the ultrasound image acquired by the image acquisition unit, a blood vessel discrimination unit (11) that discriminates whether the blood vessel detected by the blood vessel detection unit is a vein or an artery, and a discrimination execution deciding unit (15) that decides whether the blood vessel discrimination unit (11) newly executes discrimination with respect to the ultrasound image of a current frame based on a movement amount of the ultrasound probe or a change amount of the ultrasound image between frames.

14 Claims, 10 Drawing Sheets

(52) U.S. Cl.
CPC ............ *A61B 8/488* (2013.01); *A61B 8/5207* (2013.01); *A61B 8/54* (2013.01); *A61B 8/56* (2013.01); *A61B 2562/0219* (2013.01)

(58) Field of Classification Search
CPC ..... A61B 2562/0219; A61B 8/06; A61B 8/14; A61B 2560/0204; A61B 1/00025; A61B 2560/0209; A61B 1/00036; A61B 8/56; A61B 5/489

See application file for complete search history.

(56) References Cited

U.S. PATENT DOCUMENTS

| | | | |
|---|---|---|---|
| 2008/0269605 A1 | 10/2008 | Nakaya | |
| 2013/0041250 A1* | 2/2013 | Pelissier | A61B 8/4254 600/424 |
| 2014/0031690 A1* | 1/2014 | Toji | A61B 8/06 600/443 |
| 2014/0081142 A1* | 3/2014 | Toma | A61B 8/4263 600/443 |
| 2014/0343431 A1* | 11/2014 | Vajinepalli | G16H 50/30 600/454 |
| 2015/0250448 A1 | 9/2015 | Tamada | |
| 2016/0000408 A1* | 1/2016 | Matsunaga | A61B 8/463 600/443 |
| 2017/0209055 A1* | 7/2017 | Pantelopoulos | A61B 5/02438 |
| 2017/0303899 A1* | 10/2017 | Willsie | A61B 8/4254 |
| 2017/0325782 A1* | 11/2017 | Pelissier | G16H 30/20 |
| 2017/0332995 A1* | 11/2017 | Eibl | A61B 8/4427 |
| 2018/0153519 A1* | 6/2018 | Cho | A61B 8/5207 |
| 2018/0168553 A1* | 6/2018 | Hagihara | A61B 8/54 |
| 2019/0125191 A1* | 5/2019 | Siedenburg | A61B 5/6833 |
| 2021/0128101 A1* | 5/2021 | Matsumoto | A61B 8/4254 |

FOREIGN PATENT DOCUMENTS

| | | | | |
|---|---|---|---|---|
| JP | | 2017124063 A | 7/2017 | |
| WO | WO-2018134726 A1 | * | 7/2018 | ........... A61B 8/0891 |

OTHER PUBLICATIONS

International Search Report issued in PCT/JP2019/025851; mailed Sep. 17, 2019.
International Preliminary Report on Patentability and Written Opinion issued in PCT/JP2019/025851; issued Mar. 2, 2021.

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2019/025851 filed on Jun. 28, 2019, which claims priority under 35 U.S.C § 119(a) to Japanese Patent Application No. 2018-158208 filed on Aug. 27, 2018, Each of the above application(s) is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and particularly, to an ultrasound diagnostic apparatus and a method of controlling an ultrasound diagnostic apparatus that are used for observing blood vessels of a subject.

2. Description of the Related Art

In the related art, an ultrasound diagnostic apparatus has been known as an apparatus that obtains an image of the inside of a subject. Generally, the ultrasound diagnostic apparatus comprises an ultrasound probe provided with an oscillator array in which a plurality of elements are arranged. In a state where the ultrasound probe is brought into contact with a body surface of the subject, an ultrasound beam is transmitted from the oscillator array toward the inside of the subject, ultrasound echoes from the subject are received by the oscillator array, and element data are acquired. Moreover, the ultrasound diagnostic apparatus processes the obtained element data electrically, and generates an ultrasound image for a relevant part of the subject.

It is generally performed that a blood vessel of the subject is observed using such an ultrasound diagnostic apparatus. In this case, the user usually determines whether the blood vessel in the ultrasound image is a vein or an artery by visually observing the ultrasound image obtained by the ultrasound diagnostic apparatus. However, in general, it is necessary for the user to have specialized knowledge in order to visually distinguish the vein and the artery in the ultrasound image. Therefore, an ultrasound diagnostic apparatus has been developed that can discriminate whether the blood vessel in the ultrasound image is the vein or the artery even in a case where the user does not have specialized knowledge.

For example, JP2008-272025A discloses an ultrasound diagnostic apparatus that generates a so-called Doppler signal by performing frequency analysis on a received signal generated by receiving an ultrasound echo in a subject, and discriminates a blood vessel in the ultrasound image based on the intensity of the generated Doppler signal.

The ultrasound diagnostic apparatus disclosed in JP2008-272025A discriminates, among two blood vessels included in the ultrasound image, that the blood vessel having the high intensity of the Doppler signal is the artery, and the blood vessel having the low intensity of the Doppler signal is the vein.

SUMMARY OF THE INVENTION

In a case of actually observing the blood vessel using the ultrasound diagnostic apparatus, the observation is often performed while moving the ultrasound probe.

In this case, in the ultrasound diagnostic apparatus disclosed in JP2008-272025A, the ultrasound images representing different tomographic planes of the subject are sequentially generated, but a blood vessel in the ultrasound image is discriminated each time the tomographic plane of the subject represented by the ultrasound image sequentially changes, and thus there is a problem that the power consumption in the ultrasound diagnostic apparatus is large.

The present invention has been made in order to solve such related-art problems, and an object thereof is to provide an ultrasound diagnostic apparatus and a method of controlling an ultrasound diagnostic apparatus that can reduce the power consumption while discriminating the blood vessel.

In order to achieve the above object, an ultrasound diagnostic apparatus according to an aspect of the present invention comprises an ultrasound probe, an image acquisition unit that acquires an ultrasound image sequentially by transmitting an ultrasound beam toward a subject from the ultrasound probe, a blood vessel detection unit that detects a blood vessel included in the ultrasound image acquired by the image acquisition unit, a blood vessel discrimination unit that discriminates whether the blood vessel detected by the blood vessel detection unit is a vein or an artery, and a discrimination execution deciding unit that decides whether the blood vessel discrimination unit newly executes discrimination with respect to the ultrasound image of a current frame based on a movement amount of the ultrasound probe or a change amount of the ultrasound image between frames.

The ultrasound diagnostic apparatus may further comprise a motion sensor that is attached to the ultrasound probe, and a probe movement amount calculating unit that calculates the movement amount of the ultrasound probe based on a value measured by the motion sensor, in which the discrimination execution deciding unit decides whether the blood vessel discrimination unit executes discrimination based on the movement amount of the ultrasound probe calculated by the probe movement amount calculating unit.

It is preferable that the ultrasound diagnostic apparatus further comprise a discrimination result memory that holds a latest discrimination result by the blood vessel discrimination unit, in which in a case where the movement amount of the ultrasound probe calculated by the probe movement amount calculating unit is equal to or smaller than a predetermined first threshold value, the discrimination execution deciding unit decides that the blood vessel discrimination unit does not newly execute discrimination with respect to the ultrasound image of the current frame, and the blood vessel discrimination unit maintains the latest discrimination result held in the discrimination result memory.

In this case, in a case where the movement amount of the ultrasound probe calculated by the probe movement amount calculating unit is equal to or smaller than the first threshold value and larger than a second threshold value that is smaller than the first threshold value, the blood vessel discrimination unit may track a position of the blood vessel in the ultrasound image from the frame in which the blood vessel discrimination unit executes latest discrimination to the current frame, and maintain the latest discrimination result held in the discrimination result memory.

In a case where the movement amount of the ultrasound probe calculated by the probe movement amount calculating unit is larger than the first threshold value, the discrimination execution deciding unit may decide that the blood vessel discrimination unit newly executes discrimination with respect to the ultrasound image of the current frame, and the blood vessel discrimination unit may discriminate whether the blood vessel in the ultrasound image of the current frame is a vein or an artery, and update the latest discrimination result held in the discrimination result memory based on the discrimination result.

Alternatively, in a case where a state in which the movement amount of the ultrasound probe calculated by the probe movement amount calculating unit is equal to or smaller than the first threshold value continues for a predetermined time, the discrimination execution deciding unit may decide that the blood vessel discrimination unit newly executes discrimination with respect to the ultrasound image of the current frame, and the blood vessel discrimination unit may discriminate whether the blood vessel in the ultrasound image of the current frame is a vein or an artery, and update the latest discrimination result held in the discrimination result memory based on the discrimination result.

The blood vessel discrimination unit may newly execute discrimination on whether the blood vessel in the ultrasound image of the current frame is a vein or an artery after the movement amount of the ultrasound probe calculated by the probe movement amount calculating unit becomes equal to or smaller than a third threshold value that is smaller than the first threshold value.

It is preferable that the ultrasound diagnostic apparatus further comprise a display unit that displays the ultrasound image acquired by the image acquisition unit and the discrimination result held in the discrimination result memory.

It is preferable that the movement amount of the ultrasound probe calculated by the probe movement amount calculating unit include at least one of a moving speed of the ultrasound probe in parallel movement, a change amount in a movement direction of the ultrasound probe, or an angular velocity of the ultrasound probe in rotational movement.

It is preferable that the motion sensor consist of at least one of an acceleration sensor, a gyro sensor, a magnetic sensor, or a position sensor of a global positioning system.

The ultrasound diagnostic apparatus may further comprise an image change amount calculation unit that calculates the change amount of the ultrasound image between the frames by performing image analysis with respect to the ultrasound image acquired by the image acquisition unit, in which the discrimination execution deciding unit decides whether the blood vessel discrimination unit executes discrimination of the blood vessel based on the change amount of the ultrasound image calculated by the image change amount calculation unit.

It is preferable that the ultrasound diagnostic apparatus further comprise a discrimination result memory that holds a latest discrimination result of the blood vessel discrimination unit, in which in a case where the change amount of the ultrasound image between the frames calculated by the image change amount calculation unit is equal to or smaller than a predetermined fourth threshold value, the discrimination execution deciding unit decides that the blood vessel discrimination unit does not newly execute discrimination with respect to the ultrasound image of the current frame, and the blood vessel discrimination unit maintains the latest discrimination result held in the discrimination result memory.

In this case, in a case where the change amount of the ultrasound image between the frames acquired by the image change amount calculation unit is equal to or smaller than the fourth threshold value and larger than a fifth threshold value that is smaller than the fourth threshold value, the blood vessel discrimination unit may track a position of the blood vessel in the ultrasound image from the frame in which the blood vessel discrimination unit executes latest discrimination to the current frame, and maintain the latest discrimination result held in the discrimination result memory.

In a case where the change amount of the ultrasound image between the frames calculated by the image change amount calculation unit is larger than the fourth threshold value, the discrimination execution deciding unit may decide that the blood vessel discrimination unit newly executes discrimination with respect to the ultrasound image of the current frame, and the blood vessel discrimination unit may discriminate whether the blood vessel in the ultrasound image of the current frame is a vein or an artery, and update the latest discrimination result held in the discrimination result memory based on the discrimination result.

Alternatively, in a case where a state in which the change amount of the ultrasound image between the frames calculated by the image change amount calculation unit is smaller than the fourth threshold value continues for a predetermined time, the discrimination execution deciding unit may decide that the blood vessel discrimination unit newly executes discrimination with respect to the ultrasound image of the current frame, and the blood vessel discrimination unit may discriminate whether the blood vessel in the ultrasound image of the current frame is a vein or an artery, and update the latest discrimination result held in the discrimination result memory based on the discrimination result.

The blood vessel discrimination unit may newly execute discrimination on whether the blood vessel in the ultrasound image of the current frame is a vein or an artery after the change amount of the ultrasound image between the frames calculated by the image change amount calculation unit becomes equal to or smaller than a sixth threshold value that is smaller than the fourth threshold value.

It is preferable that the ultrasound diagnostic apparatus further comprise a display unit that displays the ultrasound image acquired by the image acquisition unit and the discrimination result held in the discrimination result memory.

The image acquisition unit may include a receiving unit that receives an ultrasound echo in the subject by the ultrasound probe and generates a received signal, the ultrasound diagnostic apparatus may further comprise a Doppler signal generating unit that generates a Doppler signal based on the received signal generated by the receiving unit, and the blood vessel discrimination unit may discriminate whether the blood vessel is a vein or an artery based on the Doppler signal generated by the Doppler signal generating unit.

A method of controlling an ultrasound diagnostic apparatus according to another aspect of the present invention comprises acquiring an ultrasound image sequentially by transmitting an ultrasound beam toward a subject from an ultrasound probe, detecting a blood vessel included in the acquired ultrasound image, discriminating whether the detected blood vessel is a vein or an artery, and deciding whether to newly execute discrimination with respect to the ultrasound image of a current frame based on a movement amount of the ultrasound probe or a change amount of the ultrasound image between frames.

According to the present invention, the ultrasound diagnostic apparatus comprises a blood vessel detection unit that detects a blood vessel included in the ultrasound image acquired by the image acquisition unit, a blood vessel discrimination unit that discriminates whether the blood vessel detected by the blood vessel detection unit is a vein or an artery, and a discrimination execution deciding unit that decides whether the blood vessel discrimination unit newly executes discrimination of the blood vessel included in the ultrasound image of a current frame based on a movement amount of the ultrasound probe or a change amount of the ultrasound image between frames, and thus it is possible to reduce the power consumption while discriminating the blood vessel.

DESCRIPTION OF THE PREFERRED EMBODIMENTS

Hereinafter, embodiments of the present invention will be described based on the accompanying drawings.

Embodiment 1

Figure 1:
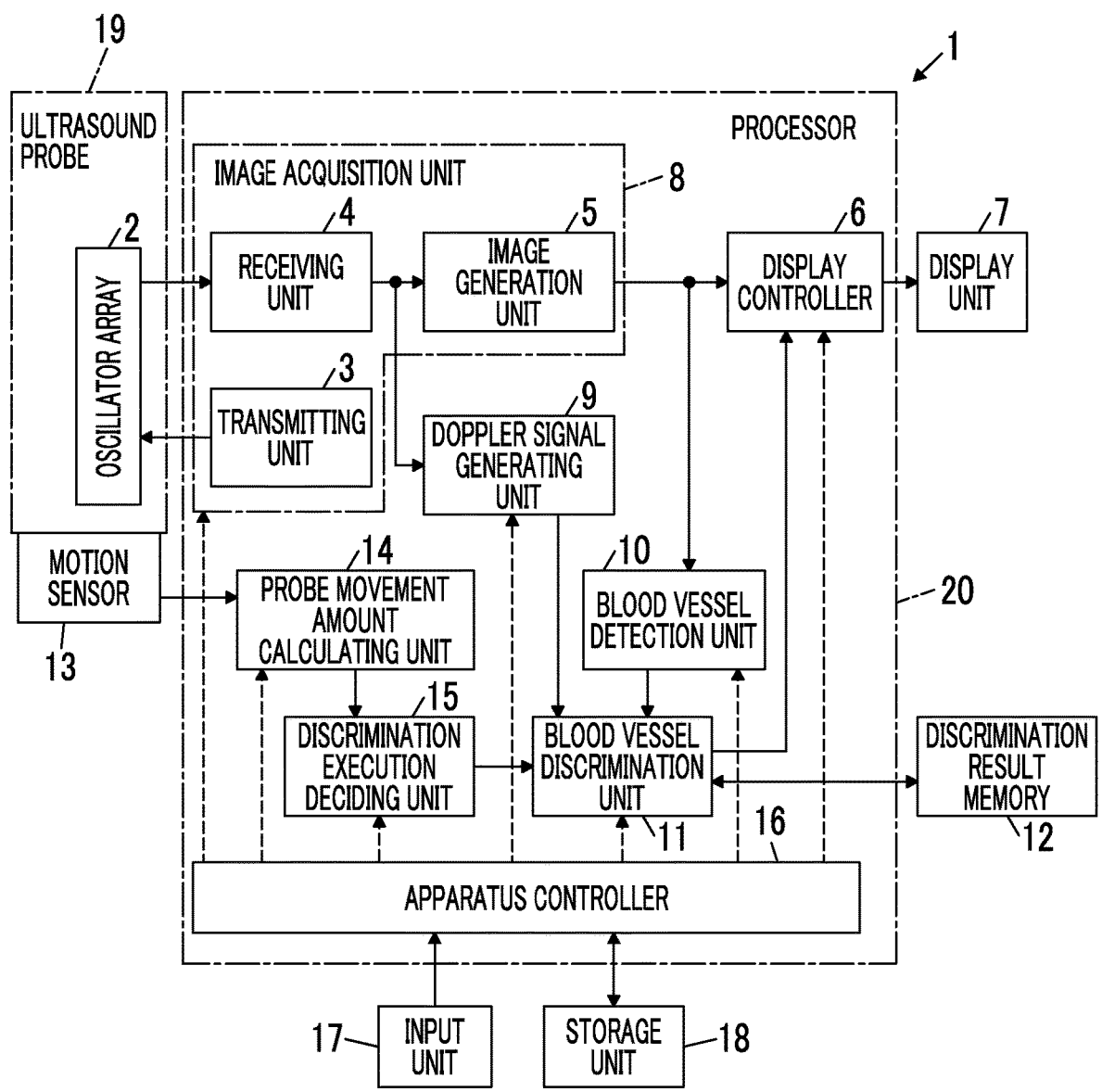
FIG. 1 is a block diagram showing a configuration of an ultrasound diagnostic apparatus according to Embodiment 1 of the present invention.

A configuration of an ultrasound diagnostic apparatus 1 according to Embodiment 1 of the present invention is shown in FIG. 1. As shown in FIG. 1, the ultrasound diagnostic apparatus 1 comprises an oscillator array 2, and a transmitting unit 3 and a receiving unit 4 are connected to the oscillator array 2. An image generation unit 5, a display controller 6, and a display unit 7 are sequentially connected to the receiving unit 4. An image acquisition unit 8 is configured by the transmitting unit 3, the receiving unit 4, and the image generation unit 5. A Doppler signal generating unit 9 is connected to the receiving unit 4. Additionally, a blood vessel detection unit 10 is connected to the image generation unit 5. A blood vessel discrimination unit 11 is connected to the Doppler signal generating unit 9 and the blood vessel detection unit 10, and a discrimination result memory 12 and the display controller 6 are connected to the blood vessel discrimination unit 11. The blood vessel discrimination unit 11 and the discrimination result memory 12 are connected to each other so as to be capable of transferring information bidirectionally. The oscillator array 2 is included in the ultrasound probe 19, and a motion sensor 13 is attached to the ultrasound probe 19. A probe movement amount calculating unit 14 is connected to the motion sensor 13, and a discrimination execution deciding unit 15 is connected to the probe movement amount calculating unit 14. The discrimination execution deciding unit 15 is connected to the blood vessel discrimination unit 11.

The apparatus controller 16 is connected to the display controller 6, the image acquisition unit 8, the Doppler signal generating unit 9, the blood vessel discrimination unit 11, the blood vessel detection unit 10, the probe movement amount calculating unit 14, and the discrimination execution deciding unit 15, and the input unit 17 and the storage unit 18 are connected to the apparatus controller 16. The apparatus controller 16 and the storage unit 18 are connected to each other so as to be capable of transferring information bidirectionally.

The processor 20 is configured by the display controller 6, the image acquisition unit 8, the Doppler signal generating unit 9, the blood vessel discrimination unit 11, the blood vessel detection unit 10, the probe movement amount calculating unit 14, the discrimination execution deciding unit 15, and the apparatus controller 16.

The oscillator array 2 of the ultrasound probe 19 shown in FIG. 1 has a plurality of oscillators arranged in one dimension or two dimensions. These oscillators transmit ultrasound waves in accordance with drive signals supplied from the transmitting unit 3, respectively, and receive ultrasound echoes from the subject to output the received signals. The respective oscillators are configured by, for example, forming electrodes to both ends of piezoelectric material made of a piezoelectric ceramic represented by lead zirconate titanate (PZT), a polymeric piezoelectric element represented by polyvinylidene difluoride (PVDF), and a piezoelectric single crystal represented by a lead magnesium niobate-lead titanate solid solution (PMN-PT).

The transmitting unit 3 of the image acquisition unit 8 includes, for example, a plurality of pulse generators, and adjust the amounts of delay of the respective drive signals to supply the adjusted drive signals to the plurality of oscillators such that the ultrasound waves transmitted from the plurality of oscillators of the oscillator array 2 form an ultrasound beam, based on a transmission delay pattern selected in accordance with the control signals from the apparatus controller 16. In this way, in a case where a pulsed or consecutive wave-like voltage is applied to electrodes of the plurality of oscillators of the oscillator array 2, the piezoelectric material expands and contracts, a pulsed or consecutive wave-like ultrasound wave is generated from the respective oscillators, and the ultrasound beam is formed from a synthetic wave of the ultrasound waves.

The transmitted ultrasound beam is reflected in, for example, targets such as a part of the subject and is propagated toward the oscillator array 2 of the ultrasound probe 19. The ultrasound echoes propagated toward the oscillator array 2 in this way are received by the respective oscillators that constitute the oscillator array 2. In this case, the respective oscillators that constitute the oscillator array 2 expand and contract by receiving the propagated ultrasound echoes, to generate electrical signals, and output the electrical signals to the receiving unit 4.

Figure 2:
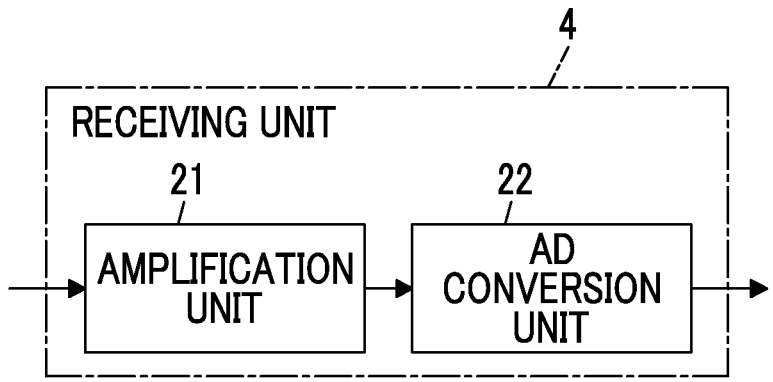
FIG. 2 is a block diagram showing an internal configuration of a receiving unit according to Embodiment 1 of the present invention.

The receiving unit 4 of the image acquisition unit 8 processes the signals output from the oscillator array 2 in accordance with the control signals from the apparatus controller 16. As shown in FIG. 2, the receiving unit 4 has a configuration that an amplification unit 21 and an analog-digital (AD) conversion unit 22 are serially connected. The amplification unit 21 amplifies the signals input from the respective oscillators that constitute the oscillator array 2, and transmits the amplified signals to the AD conversion unit 22. The AD conversion unit 22 converts the signals transmitted from the amplification unit 21 into digitalized received signal, and sends the data to the image generation unit 5 of the image acquisition unit 8.

Figure 3:
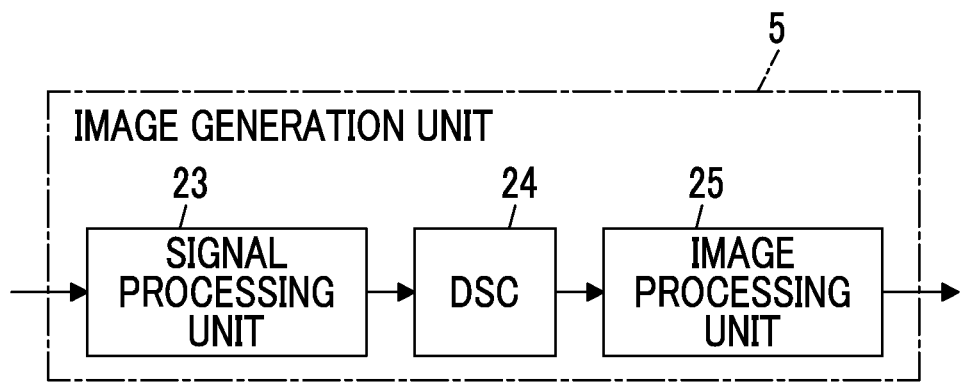
FIG. 3 is a block diagram showing an internal configuration of an image generation unit according to Embodiment 1 of the present invention.

As shown in FIG. 3, the image generation unit 5 of the image acquisition unit 8 has a configuration that a signal processing unit 23, a digital scan converter (DSC) 24, and an image processing unit 25 are serially connected. The signal processing unit 23 performs reception focus processing that addition (phasing addition) is performed by giving each delay to each data of the received signals, based on a reception delay pattern selected in accordance with the control signals from the apparatus controller 16. With the reception focus processing, sound ray signals in which focal points of the ultrasound echoes are narrowed to one scan line are generated. Additionally, the signal processing unit 23 subjects the generated sound ray signals to the correction of damping resulting from a propagation distance depending on the depth at a position where the ultrasound waves are reflected, and then performs envelope detection processing to generate B-mode image signals indicating a tissue within the subject. The B-mode image signals generated in this way are output to the DSC 24.

The DSC 24 of the image generation unit 5 raster-converts the B-mode image signals into image signals based on a scan mode of normal television signals to generate the ultrasound image. The image processing unit 25 of the image generation unit 5 subjects the ultrasound image obtained in the DSC 24 to various kinds of required image processing such as brightness correction, grayscale correction, sharpness correction, and color correction, and then outputs an ultrasound image to the display controller 6, and the blood vessel detection unit 10.

Figure 4:
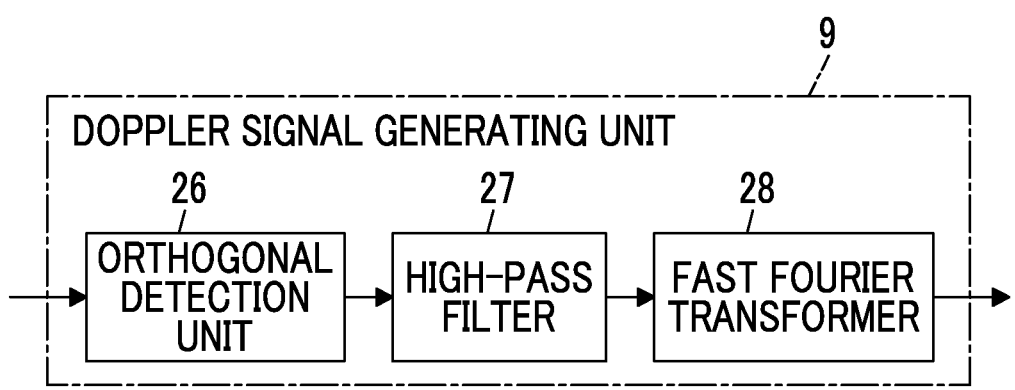
FIG. 4 is a block diagram showing an internal configuration of a Doppler signal generating unit according to Embodiment 1 of the present invention.

The Doppler signal generating unit 9 of the processor 20 generates the Doppler signal by a so-called pulse Doppler method. As shown in FIG. 4, the Doppler signal generating unit 9 has a configuration in which an orthogonal detection unit 26, a high-pass filter 27, a fast Fourier transformer 28 are sequentially connected in series.

The orthogonal detection unit 26 orthogonally detects the received signal and converts the received signal into complex data by mixing the carrier signal of the reference frequency with the received signal generated by the receiving unit 4.

The high-pass filter 27 functions as a so-called wall filter, and removes frequency components derived from the movement of the body tissue of the subject from the complex data generated by the orthogonal detection unit 26.

The fast Fourier transformer 28 performs frequency analysis by Fourier transforming the complex data of a plurality of sample points, and generates the Doppler signal representing a so-called spectrum.

Figure 5:
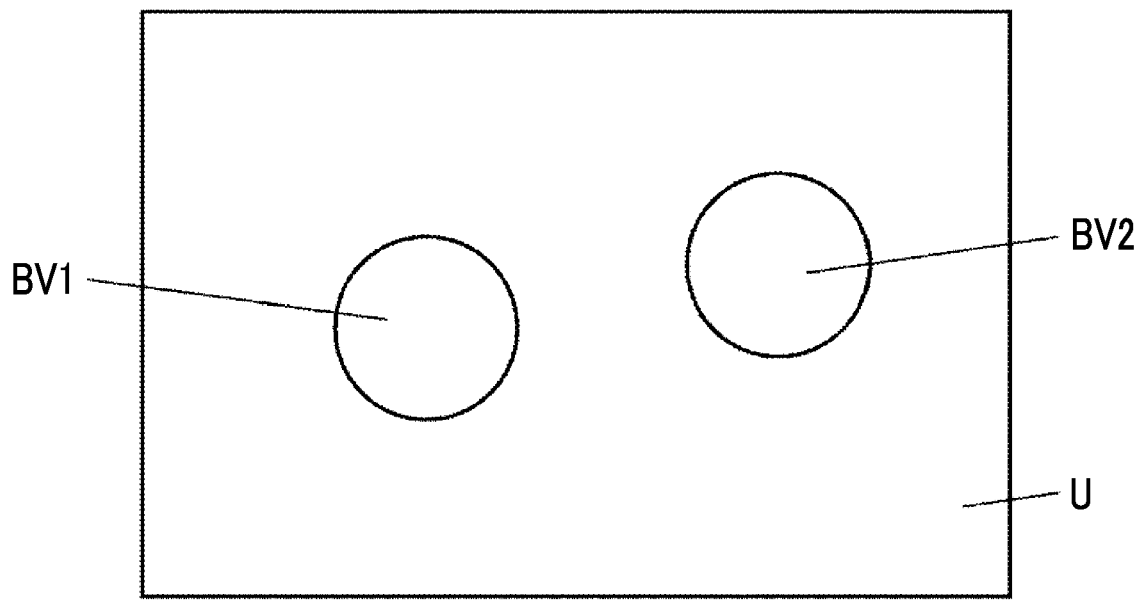
FIG. 5 is a diagram schematically showing an ultrasound image including a cross section of a blood vessel.

The blood vessel detection unit 10 of the processor 20 performs image analysis with respect to the ultrasound image acquired by the image acquisition unit 8, and detects the blood vessel included in the ultrasound image. For example, as shown in FIG. 5, the blood vessel detection unit 10 detects cross sections of blood vessels BV1 and BV2 included in the ultrasound image U.

The cross section of the blood vessel represents the section of the blood vessel in a case of cutting the blood vessel across a central axis thereof. More specifically, for example, the blood vessel detection unit 10 can detect the cross section of the blood vessel by storing typical pattern data as a template in advance, calculating the similarity to the pattern data while searching the image with the template, and assuming the blood vessel is present in the position where the similarity is equal to or larger than a threshold value and is maximum.

A machine learning method described in Csurka et al.: Visual Categorization with Bags of Keypoints, Proc. of ECCV Workshop on Statistical Learning in Computer Vision, pp. 59-74 (2004), a general image recognition method using deep learning described in Krizhevsky et al.: Image Net Classification with Deep Convolutional Neural Networks, Advances in Neural Information Processing Systems 25, and pp. 1106-1114 (2012), or the like can be used for the calculation of the similarity in addition to the simple template matching.

The motion sensor 13 attached to the ultrasound probe 19 measures the movement of the ultrasound probe 19 moved by the user. Examples of the motion sensor 13 include an acceleration sensor, a gyro sensor, a magnetic sensor, or a position sensor of a global positioning system (GPS). Therefore, the motion sensor 13 measures acceleration of the ultrasound probe 19 in parallel movement, angular acceleration or an angular velocity of the ultrasound probe 19 in rotational movement, and position of the ultrasound probe 19 as the movement of the ultrasound probe 19.

The probe movement amount calculating unit 14 of the processor 20 calculates the movement amount of the ultrasound probe 19 based on the value measured by the motion sensor 13. The probe movement amount calculating unit 14 can calculate a moving speed of the ultrasound probe 19 in parallel movement, an angular velocity of the ultrasound probe 19 in rotational movement, and the change amount in the movement direction of the ultrasound probe 19 as the movement amount of the ultrasound probe 19.

The blood vessel discrimination unit 11 of the processor 20 discriminates whether the blood vessels BV1 and BV2 detected by the blood vessel detection unit 10 are the vein or the artery. In general, the artery beats at a constant cycle, the intensity of the Doppler signal in the cross section of the blood vessel corresponding to the artery also changes at the same constant cycle as the beat. On the other hand, the vein does not beat, and thus the intensity of the Doppler signal in the cross section of the blood vessel corresponding to the vein does not change periodically. Therefore, for example, the blood vessel discrimination unit 11 discriminates that the blood vessel in which the intensity of the Doppler signal generated by the Doppler signal generating unit 9 changes periodically is the artery, and the blood vessel in which the intensity of the Doppler signal does not change periodically is vein.

It is preferable that the blood vessel be discriminated in a state where the ultrasound probe 19 is substantially stationary such that the blood vessels can be accurately discriminated. Therefore, it is desirable that the blood vessel discrimination unit 11 discriminates the blood vessel after the movement amount of the ultrasound probe 19 calculated by the probe movement amount calculating unit 14 is in a substantially stationary state.

Figure 6:
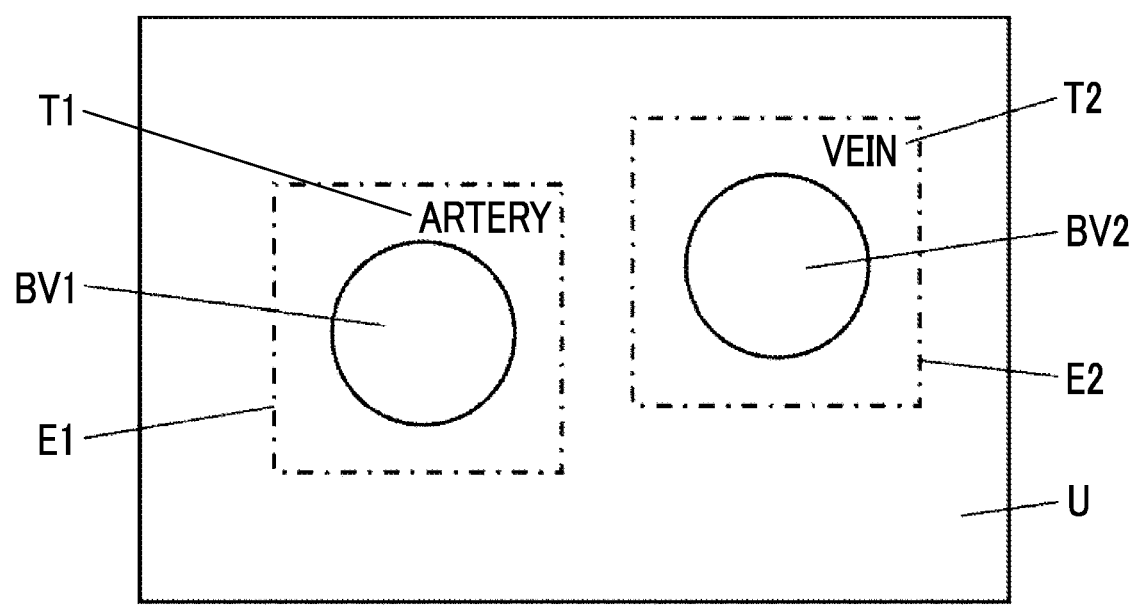
FIG. 6 is a diagram schematically showing a discrimination result of the blood vessel.

In addition, the blood vessel discrimination unit 11 causes the display unit 7 to display the discrimination results for the blood vessels BV1 and BV2 via the display controller 6. For example, as shown in FIG. 6, the blood vessel discrimination unit 11 can display the discrimination results that the blood vessel BV1 is the artery and the blood vessel BV2 is the vein on the display unit 7 by discriminating that the blood vessel BV1 is the artery and the blood vessel BV2 is the vein, displaying a text T1 indicating that the blood vessel is the artery and a surrounding line E1 surrounding the blood vessel BV1 and the text T1 in the vicinity of the blood vessel BV1 in the ultrasound image U, and displaying a text T2 indicating that the blood vessel is the vein and a surrounding line E2 surrounding the blood vessel BV2 and the text T2 in the vicinity of the blood vessel BV2. In this case, for example, the blood vessel discrimination unit 11 can display the surrounding lines E1 and E2 with different colors such as red and blue on the display unit 7 such that the user can easily confirm whether the blood vessels BV1 and the BV2 are the vein or the artery.

The discrimination result memory 12 of the ultrasound diagnostic apparatus 1 stores the latest discrimination result by the blood vessel discrimination unit 11. As the discrimination result memory 12, a recording medium such as a hard disc drive (HDD), a solid state drive (SSD), a flexible disc (FD), a magneto-optical (MO) disc, a magnetic tape (MT), a random access memory (RAM), a compact disc (CD), a digital versatile disc (DVD), a secure digital (SD) card, a universal serial bus (USB) memory, or the like, or a server can be used. The discrimination result memory 12 is not included in the processor 20, but may be included in the processor 20.

The discrimination execution deciding unit 15 of the processor 20 decides whether the blood vessel discrimination unit 11 newly executes discrimination of the blood vessel included in the ultrasound image of the current frame acquired by the image acquisition unit 8 based on the movement amount of the ultrasound probe 19 calculated by the probe movement amount calculating unit 14. For example, the discrimination execution deciding unit 15 decides that discrimination of the blood vessel is not newly executed with respect to the ultrasound image of the current frame in a case where the movement amount of the ultrasound probe 19 calculated by the probe movement amount calculating unit 14 is equal to or smaller than a predetermined first threshold value, and decides that discrimination of the blood vessel is newly executed with respect to the ultrasound image of the current frame in a case where the movement amount of the ultrasound probe 19 is larger than the first threshold value. For example, in a case where the movement amount of the ultrasound probe 19 is the moving speed of the ultrasound probe 19 in parallel movement, 20 mm/sec can be set as the first threshold value.

As a result, it is possible to prevent the blood vessel discrimination unit 11 from performing unnecessary discrimination processing, reduce the calculation load on the ultrasound diagnostic apparatus 1, and further reduce the power consumption on the ultrasound diagnostic apparatus 1.

The apparatus controller 16 of the processor 20 performs control of the respective units of the ultrasound diagnostic apparatus 1 based on the programs that are stored in advance in the storage unit 18 and the like and the operation of the user via the input unit 17.

Under the control of the apparatus controller 16, the display controller 6 of the processor 20 performs predetermined processing on an ultrasound image generated by the image generation unit 5 of the image acquisition unit 8, and displays the ultrasound image on the display unit 7.

The display unit 7 of the ultrasound diagnostic apparatus 1 displays the ultrasound image under the control of the display controller 6, and includes display devices such as a liquid crystal display (LCD), and an organic electroluminescence (EL) display.

The input unit 17 of the ultrasound diagnostic apparatus 1 is a device for the user to perform input operation, and can be configured to comprise a keyboard, a mouse, a trackball, a touchpad, a touch panel, and the like.

The storage unit 18 stores the operating program of the ultrasound diagnostic apparatus 1, and as the storage unit, a recording medium such as the HDD, the SSD, the FD, the MO disc, the MT, the RAM, the CD, the DVD, the SD card, the USB memory, or the like can be used similarly to the discrimination result memory 12.

In addition, the processor 20 having the display controller 6, the image acquisition unit 8, the Doppler signal generating unit 9, the blood vessel discrimination unit 11, the blood vessel detection unit 10, the probe movement amount calculating unit 14, the discrimination execution deciding unit 15, and the apparatus controller 16 is configured from a central processing unit (CPU) and control programs for making the CPU perform various kinds of processing. However, the processor 20 may be configured from a field programmable gate array (FPGA), a digital signal processor (DSP), an application specific integrated circuit (ASIC), or other integrated circuits (ICs), or may be configured by combining them.

The configuration can be adopted in which the display controller 6, the image acquisition unit 8, the Doppler signal generating unit 9, the blood vessel discrimination unit 11, the blood vessel detection unit 10, the probe movement amount calculating unit 14, the discrimination execution deciding unit 15, and the apparatus controller 16 of the processor 20 are partially or entirely integrated into one CPU.

Next, the operation of the ultrasound diagnostic apparatus 1 in Embodiment 1 will be described in detail using a flowchart shown in FIG. 7. In the following operation description, the image acquisition unit 8 of the processor 20 sequentially and consecutively acquires the ultrasound images and displays the ultrasound images on the display unit 7, and the user moves the ultrasound probe 19 as the blood vessel is observed.

First, in step S1, the probe movement amount calculating unit 14 calculates the movement amount of the ultrasound probe 19 based on the measured value obtained by the motion sensor 13 attached to the ultrasound probe 19.

Next, in step S2, the blood vessel discrimination unit 11 determines whether the ultrasound probe 19 is in a substantially stationary state, that is, whether the movement amount of the ultrasound probe 19 calculated in step S1 is equal to or smaller than the third threshold value that is smaller than the first threshold value. For example, in a case where the movement amount of the ultrasound probe 19 is the moving speed of the ultrasound probe 19 in parallel movement, 3 mm/sec can be set as the third threshold value. In step S2, in a case where the determination is made that the movement amount of the ultrasound probe 19 is larger than the third threshold value, the process returns to step S1, the movement amount of the ultrasound probe 19 is newly calculated, and the process proceeds to step S2. As described above, step S1 and step S2 are repeated until the movement amount of the ultrasound probe 19 become equal to or smaller than the third threshold value.

In a case where the determination is made that the movement amount of the ultrasound probe 19 is equal to or smaller than the third threshold value in step S2, the process proceeds to step S3. In step S3, the blood vessel detection unit 10 performs image analysis with respect to the ultrasound image of the current frame acquired by the image acquisition unit 8, and performs detection processing of the blood vessels BV1 and BV2 included in the ultrasound image U is performed as shown in FIG. 5, for example.

In following step S4, the blood vessel discrimination unit 11 performs processing of discriminating whether the blood vessels BV1 and BV2 are the vein or the artery based on the intensity of the Doppler signal in the blood vessels BV1 and BV2 detected in step S3. For example, it is possible that the Doppler signal generating unit 9 generates the Doppler signal corresponding to entire area of the ultrasound image U, and the blood vessel discrimination unit 11 discriminates that among the blood vessels BV1 and BV2, the blood vessel in which the intensity of the Doppler signal changes periodically is the artery, and the blood vessel in which the intensity of the Doppler signal does not change periodically is vein. In a case where the Doppler signal corresponding to the entire area of the ultrasound image U is obtained by the Doppler signal generating unit 9, the oscillator array 2 of the ultrasound probe 19 transmits the ultrasound beam to the cross section of the subject corresponding to the entire area of the ultrasound image U.

In step S5, the blood vessel discrimination unit 11 holds the discrimination result obtained in step S4 in the discrimination result memory 12.

In step S6, the blood vessel discrimination unit 11 displays the discrimination result held in the discrimination result memory 12 in step S5 on the display unit 7. For example, as shown in FIG. 6, the blood vessel discrimination unit 11 can display the discrimination results on the display unit 7 by displaying a text T1 indicating that the blood vessel is the artery and a surrounding line E1 surrounding the blood vessel BV1 and the text T1 in the vicinity of the blood vessel BV1, and displaying a text T2 indicating that the blood vessel is the vein and a surrounding line E2 surrounding the blood vessel BV2 and the text T2 in the vicinity of the blood vessel BV2 while being superimposed on the ultrasound image U.

In the following step S7, it is determined whether the operation of the ultrasound diagnostic apparatus 1 ends. For example, although not shown, in a case where a operation end button for ending the operation of the ultrasound diagnostic apparatus 1 is displayed on the display unit 7, and the user presses the operation end button via the input unit 17, it is determined that the operation of the ultrasound diagnostic apparatus 1 ends, and thus the operation of the ultrasound diagnostic apparatus 1 ends. In a case where the operation end button is not pressed, it is determined that the operation of the ultrasound diagnostic apparatus 1 does not end, and the process proceeds to step S8.

In step S8, the probe movement amount calculating unit 14 newly calculates the movement amount of the ultrasound probe 19 in the same manner as in step S1.

In following step S9, the discrimination execution deciding unit 15 determines whether the movement amount of the ultrasound probe 19 calculated in step S8 is larger than the first threshold value. In a case where the determination is made that the movement amount of the ultrasound probe 19 is equal to or smaller than the first threshold value in step S9, the process proceeds to step S10. In step S10, the discrimination execution deciding unit 15 decides that the blood vessel discrimination unit 11 does not newly discriminate the blood vessel in the ultrasound image of the current frame.

Figure 8:
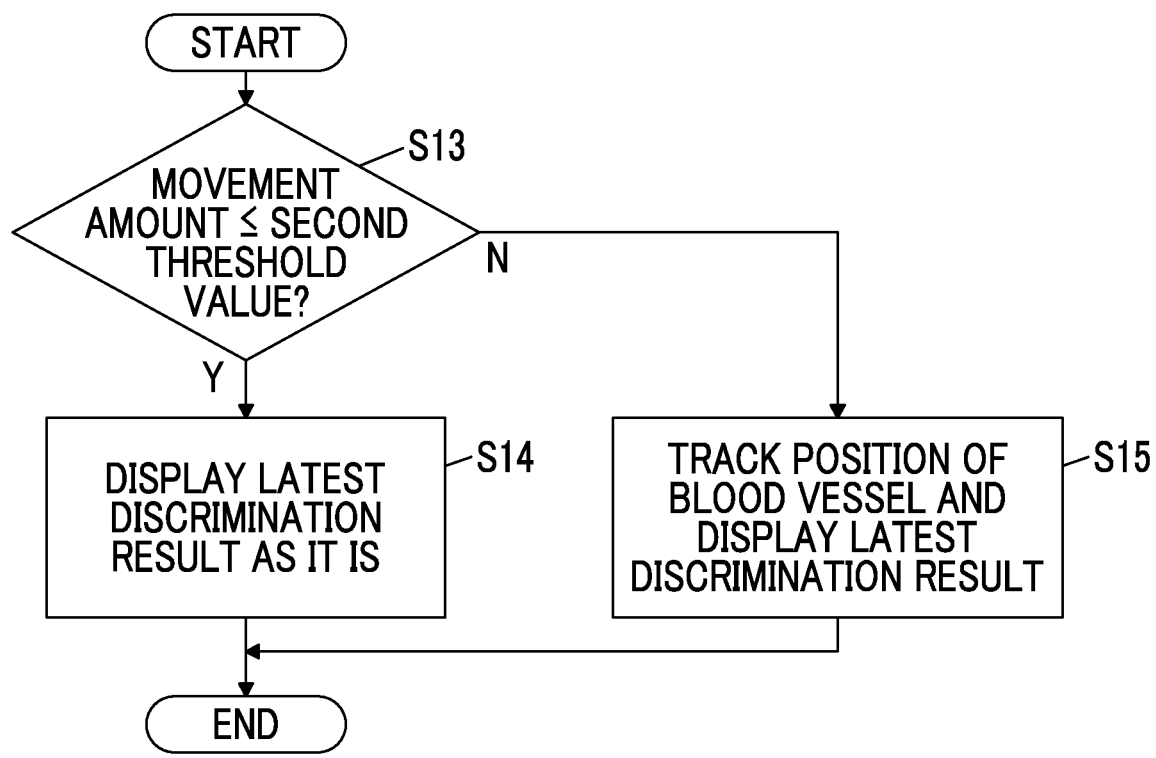
FIG. 8 is a flowchart showing an operation of displaying the latest discrimination result in Embodiment 1 of the present invention.

In following step S11, the blood vessel discrimination unit 11 displays the latest discrimination result, that is, the discrimination result held in step S5 while being superimposed on the ultrasound image U. The detailed operation in step S11 will be described with reference to the flowchart of FIG. 8. Step S11 is processing executed in a case where the determination is made that the movement amount of the ultrasound probe 19 is equal to or smaller than the first threshold value in step S9, and includes three steps of step S13 to step S15 as shown in FIG. 8.

First, in step S13, the blood vessel discrimination unit 11 determines whether the movement amount of the ultrasound probe 19 calculated in step S8 is equal to or smaller than a predetermined second threshold value. The second threshold value is a value smaller than the first threshold value and equal to or larger than the third threshold value. In a case where the determination is made that the movement amount of the ultrasound probe 19 is equal to or smaller than the second threshold value in step S13, the process proceeds to step S14.

In step S14, the blood vessel discrimination unit 11 determines that the ultrasound probe 19 is in a substantially stationary state, and in step S5, the discrimination result held in the discrimination result memory 12 is maintained. Further, the blood vessel discrimination unit 11 displays the discrimination results for the blood vessels corresponding to the blood vessels BV1 and BV2 shown in FIGS. 5 and 6 held in the discrimination result memory 12 in step S5 while being superimposed on the ultrasound image of the current frame. In a case where processing of step S14 is completed, the processing of step S11 ends.

Also, in a case where the determination is made that the movement amount of the ultrasound probe 19 is larger than the second threshold value in step S13, the process proceeds to step S15.

In step S15, the blood vessel discrimination unit 11 determines that the ultrasound probe 19 has movement, but has no big movement as to newly perform discrimination processing, tracks the blood vessels BV1 and BV2 included in the ultrasound image U, and maintains the discrimination result held in the discrimination result memory 12 in step S5. Further, the blood vessel discrimination unit 11 performs processing of displaying the discrimination results for the blood vessels corresponding to the blood vessels BV1 and BV2 included in the ultrasound image U held in the discrimination result memory 12.

Figure 9:
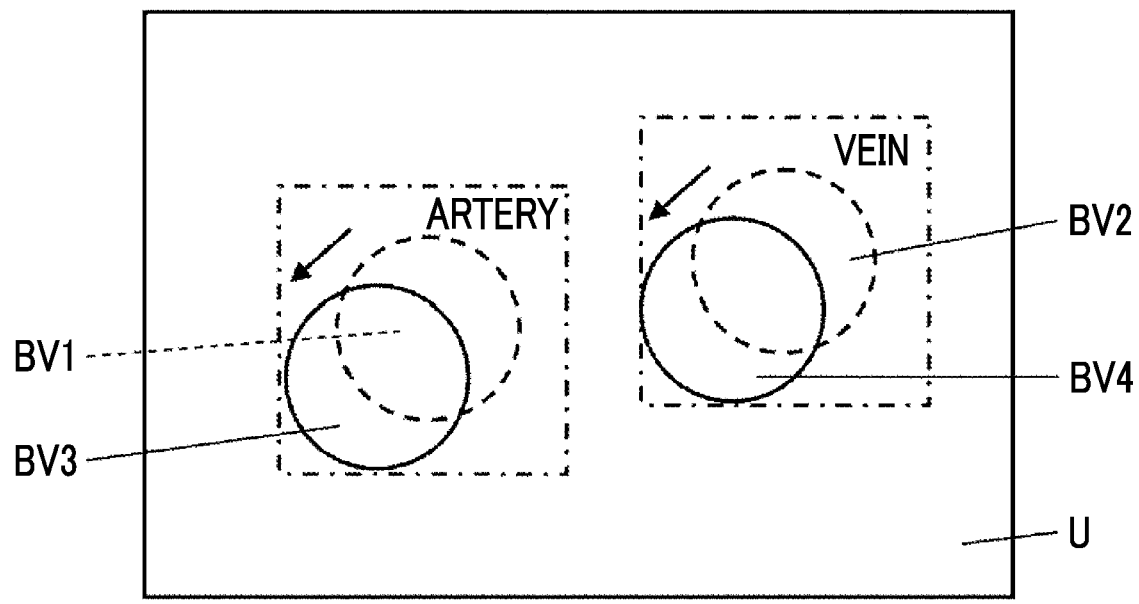
FIG. 9 is a diagram schematically showing a state in which the position of the blood vessel is moved in the ultrasound image.
Figure 10:
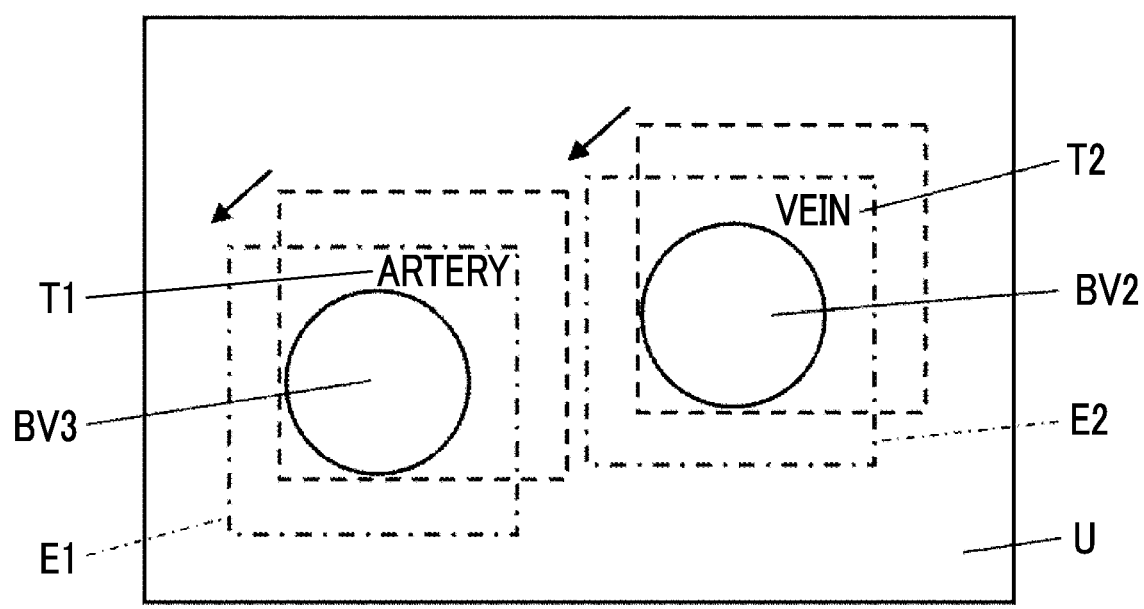
FIG. 10 is a diagram schematically showing a state in which the position of blood vessel in the ultrasound image is tracked and the latest discrimination result is displayed.

For example, the user moves the ultrasound probe 19 by the movement amount that is equal to or smaller than the first threshold value and larger than the second threshold value, and as shown in FIG. 9, in a case where the blood vessels BV1 and BV2 in the ultrasound image U is moved to blood vessels BV3 and BV4, the blood vessel discrimination unit 11 can display the texts T1 and T2, and the surrounding lines E1 and E2 on the display unit 7 in a state where the texts T1 and T2, and the surrounding lines E1 and E2 are moved in accordance with the movement of the blood vessels BV1 and BV2 in the ultrasound image U, as shown in FIG. 10. As described above, the blood vessel discrimination unit 11 tracks the position of the blood vessel, and displays the discrimination results for the blood vessels BV3 and BV4 of the current frame held in step S5 which correspond to the blood vessels BV1 and BV2 of the frame in which the latest discrimination is performed. For example, the blood vessel discrimination unit 11 can track the blood vessels BV1 and BV2 by performing matching between the frames adjacent to each other in time series, and a so-called optical flow method.

In a case where processing of step S15 is completed, the processing of step S11 ends.

In this way, in a case where the latest discrimination result held in step S5 is displayed on the display unit 7 in step S11, the process returns to step S7. In a case where the determination is made that the operation of the ultrasound diagnostic apparatus 1 ends in step S7, the operation of the ultrasound diagnostic apparatus 1 ends. In a case where the determination is made that the operation of the ultrasound diagnostic apparatus 1 does not end in step S7, the process proceeds to step S8, and the movement amount of the ultrasound probe 19 is calculated. In following step S9, the determination is made on whether the movement amount of the ultrasound probe 19 calculated in step S8 is larger than the first threshold value. In a case where the determination is made that the movement amount of the ultrasound probe 19 is equal to or smaller than the first threshold value in step S9, the process proceeds to step S10.

As described above, until the determination is made on whether the operation of the ultrasound diagnostic apparatus 1 ends in step S7 or the determination is made that the movement amount of the ultrasound probe 19 calculated in preceding step S8 is larger than the first threshold value in step S9, the processing items of step S7 to step S11 are repeated.

Also, in a case where the determination is made that the movement amount of the ultrasound probe 19 calculated in step S8 is larger than the first threshold value in step S9, the process proceeds to step S12. In step S12, the discrimination execution deciding unit 15 decides that the blood vessel discrimination unit 11 newly execute discrimination with respect to the ultrasound image of the current frame. As described above, in a case where the processing of step S12 is completed, the process returns to step S1, and the probe movement amount calculating unit 14 calculates the movement amount of the ultrasound probe 19.

In following step S2, the blood vessel detection unit 10 determines whether the movement amount of the ultrasound probe 19 calculated in step S1 is equal to or smaller than the third threshold value. In a case where the determination is made that the movement amount of the ultrasound probe 19 is larger than the third threshold value in step S2, the process returns to step S1. In a case where the determination is made that the movement amount of the ultrasound probe 19 is equal to or smaller than the third threshold value in step S2, the process proceeds to step S3.

In step S3, the blood vessel detection unit 10 newly detects the blood vessel by performing image analysis with respect to the ultrasound image of the current frame.

In step S4, the blood vessel discrimination unit 11 newly discriminates whether the blood vessel newly detected in step S3 is the vein or the artery.

In step S5, the blood vessel discrimination unit 11 updates the discrimination result held in the discrimination result memory 12 using the new discrimination result obtained in step S4. That is, the blood vessel discrimination unit 11 overwrites the discrimination result previously held in the discrimination result memory 12, and holds the new discrimination result obtained in step S4 in the discrimination result memory 12.

In following step S6, the blood vessel discrimination unit 11 displays the discrimination result updated in step S5 while being superimposed on the ultrasound image of the current frame.

In a case where the processing of step S6 is completed, the process proceeds to step S7, and it is determined whether the operation of the ultrasound diagnostic apparatus 1 ends. In step S7, in a case where the determination is made that the operation of the ultrasound diagnostic apparatus 1 does not end, the process proceeds to step S8, and in a case where the determination is made than the operation of the ultrasound diagnostic apparatus 1 ends, the operation of the ultrasound diagnostic apparatus 1 ends.

As described above, in the ultrasound diagnostic apparatus 1 according to Embodiment 1, the blood vessel detection unit 10 automatically detects the blood vessels BV1 and BV2 in the ultrasound image U, the blood vessel discrimination unit 11 discriminates whether the detected blood vessels BV1 and BV2 are the vein or the artery, and the discrimination execution deciding unit 15 decides whether the blood vessel discrimination unit 11 executes discrimination of the blood vessels BV1 and BV2 based on the movement amount of the ultrasound probe 19, and thus by not performing unnecessary discrimination processing with respect to the blood vessels BV1 and BV2 in a case where the movement amount of the ultrasound probe 19 is equal to or smaller than the first threshold value, it is possible to reduce the power consumption of the ultrasound diagnostic apparatus 1 while discriminating the blood vessels BV1 and BV2.

In particular, in a portable ultrasound diagnostic apparatus using a battery as a drive power source, it is preferable to reduce the power consumption as much as possible and secure the driving time, and thus it is greatly useful to apply the aspect of Embodiment 1 of the present invention.

In an example shown in FIG. 6 of Embodiment 1, the rectangular surrounding lines E1 and E2 are displayed while being superimposed on the ultrasound image U, but the shapes of the surrounding lines E1 and E2 are not particularly limited as long as the blood vessel BV1 is surrounded by the surrounding line E1, and the blood vessel BV2 is surrounded by the surrounding line E2. For example, the surrounding lines E1 and E2 can each have any closed shape such as a circular shape or a polygonal shape.

As shown in FIG. 6, the blood vessel discrimination unit 11 displays the text T1 and the surrounding line E1 in the vicinity of the blood vessel BV1, and the text T2 and the surrounding line E2 in the vicinity of the blood vessel BV2, but also can display only the text T1 and the text T2 while being superimposed on the ultrasound image U.

In Embodiment 1, the Doppler signal generating unit 9 generates the Doppler signal corresponding to the entire area of the ultrasound image U, but can generate the Doppler signal corresponding to a part of the ultrasound image U including the blood vessels BV1 and BV2. For example, although not shown, the Doppler signals corresponding to a first region of interest and a second region of interest are generated by setting the first region of interest including only the blood vessel BV1 and the second region of interest including the blood vessel BV2, and transmitting the ultrasound beam from the oscillator array 2 of the ultrasound probe 19 with respect to the cross section of the subject corresponding to the first region of interest and the second region of interest of the ultrasound image U. As a result, it is possible to reduce the calculation load in the Doppler signal generating unit 9 in a case of generating the Doppler signal, and further reduce the power consumption of the ultrasound diagnostic apparatus 1.

In Embodiment 1, the blood vessel discrimination unit 11 discriminates whether the blood vessels BV1 and BV2 are the vein or the artery based on the intensity of the Doppler signal in the blood vessels BV1 and BV2, but the discrimination method of the blood vessel is not particularly limited thereto. In general, the diameter of the vein is smaller than the diameter of the artery, the vascular wall of the vein is thinner than the vascular wall of the artery, and the circularity of the cross section of the vein is lower than the circularity of the cross section of the artery, and thus the blood vessel discrimination unit 11 can discriminate the vein and the artery based on the diameters of the blood vessels BV1 and BV2 included in the ultrasound image U, the thicknesses of the vascular walls of the blood vessels BV1 and BV2, and the circularities of the cross sections of the blood vessels BV1 and BV2.

Embodiment 2

Figure 7:
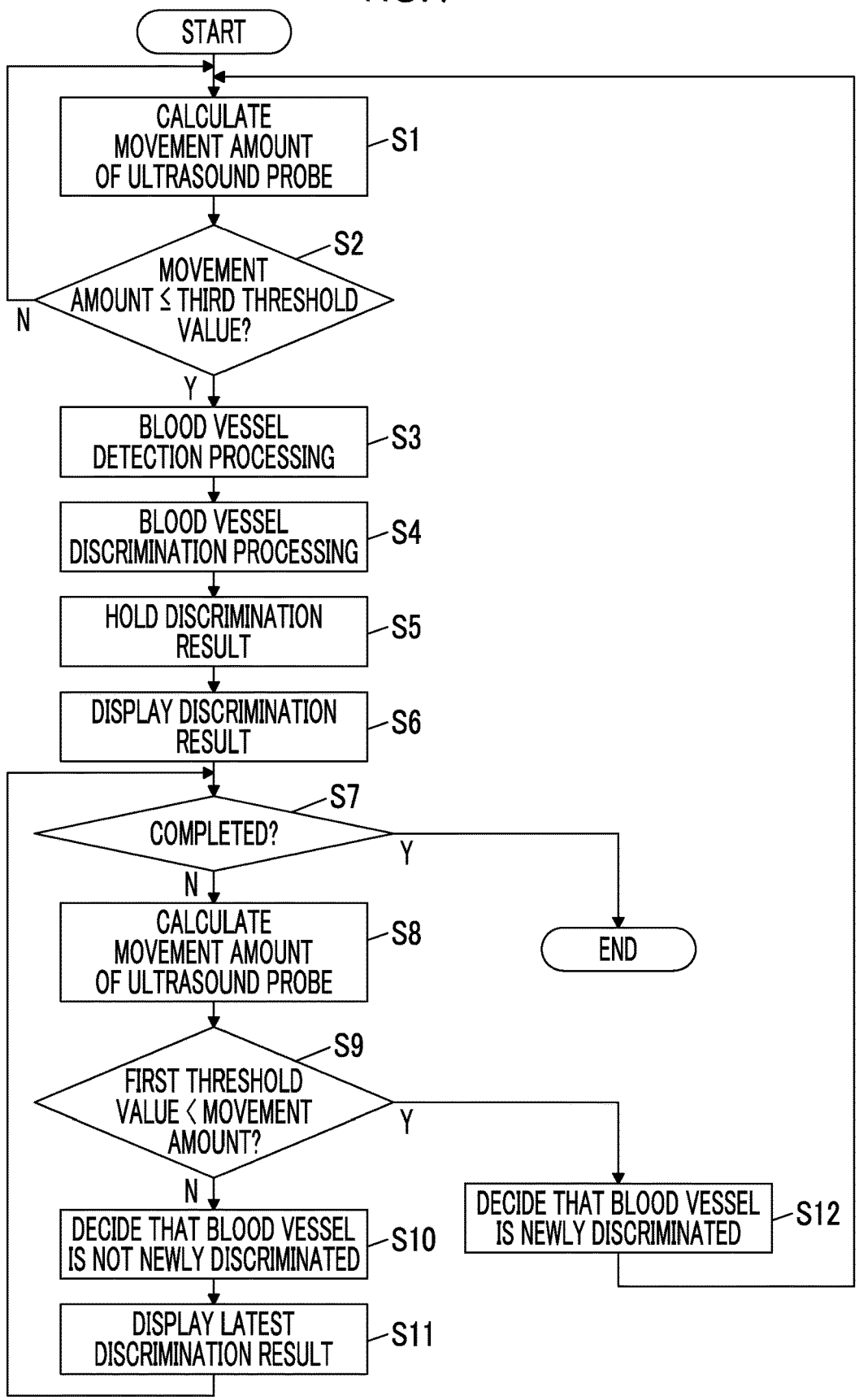
FIG. 7 is a flowchart showing an operation of the ultrasound diagnostic apparatus according to Embodiment 1 of the present invention.

In Embodiment 1, only in a case where the determination is made that the movement amount of the ultrasound probe 19 calculated by the probe movement amount calculating unit 14 is larger than a predetermined first threshold value in step S9 of the flowchart shown in FIG. 7, the discrimination execution deciding unit 15 decides that the blood vessel discrimination unit 11 newly discriminates blood vessel in step S12, but the discrimination execution deciding unit 15 can also decide that the blood vessel discrimination unit 11 newly executes discrimination, for example, in a case where a state in which the movement amount of the ultrasound probe 19 is equal to or smaller than the first threshold value continues for a predetermined time.

Figure 11:
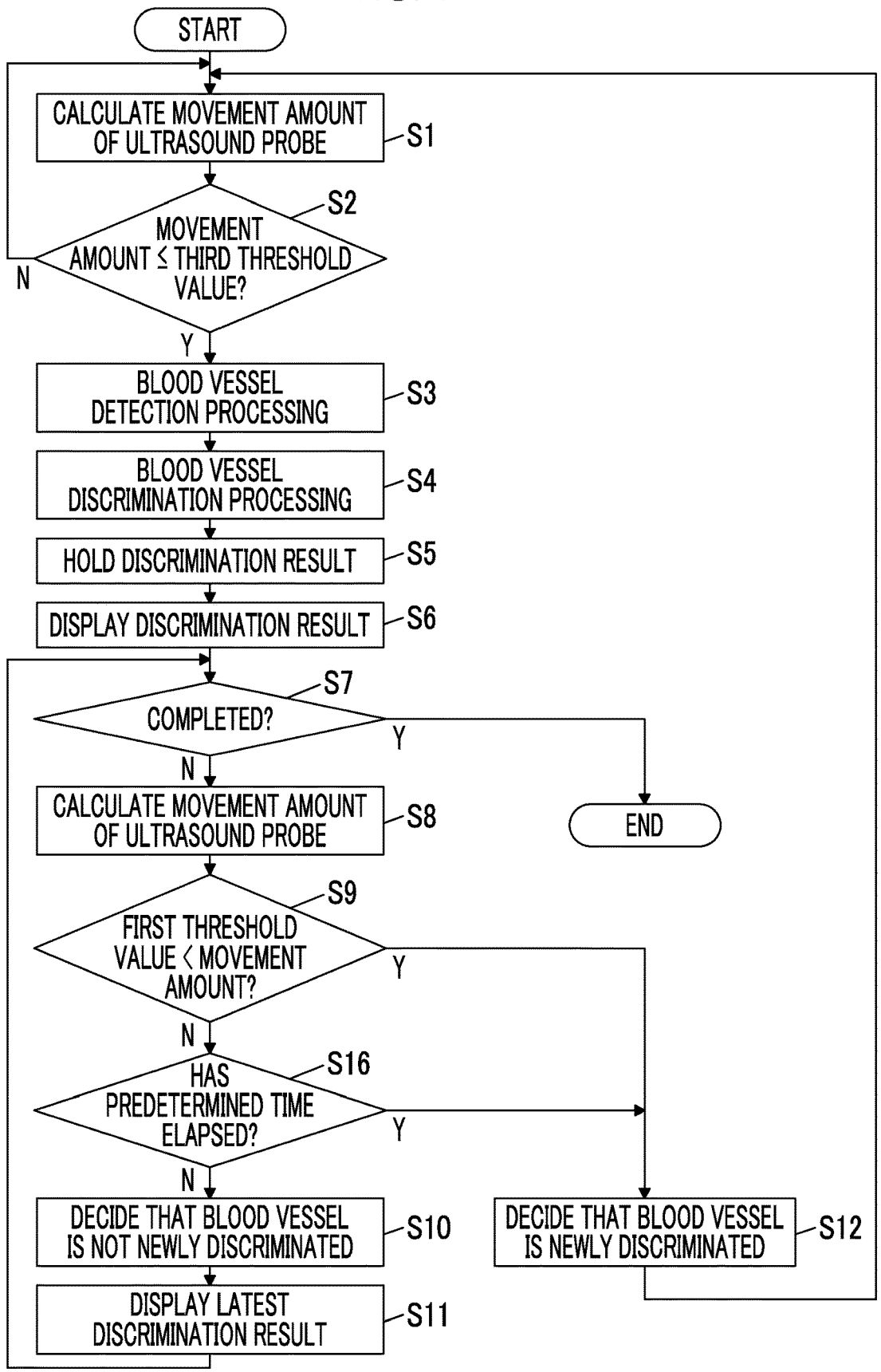
FIG. 11 is a flowchart showing an operation of the ultrasound diagnostic apparatus according to Embodiment 2 of the present invention.

The operation of the ultrasound diagnostic apparatus 1 in Embodiment 2 will be described using a flowchart shown in FIG. 11. The flowchart of FIG. 11 is a flowchart in which step S16 is added between step S9 and step S10 of the flowchart of Embodiment 1 shown in FIG. 7.

First, in step S1, the probe movement amount calculating unit 14 calculates the movement amount of the ultrasound probe 19 based on the measured value measured by the motion sensor 13 attached to the ultrasound probe 19.

In following step S2, the blood vessel detection unit 10 determines whether the movement amount of the ultrasound probe 19 calculated in step S1 is equal to or smaller than the third threshold value. In a case where the determination is made that the movement amount of the ultrasound probe 19 is larger than the third threshold value in step S2, the process returns to step S1. In a case where the determination is made that the movement amount of the ultrasound probe 19 is equal to or smaller than the third threshold value in step S2, the process proceeds to step S3.

In step S3, the blood vessel detection unit 10 detects the blood vessels BV1 and BV2 included in the ultrasound image U is performed, for example, as shown in FIG. 5 by performing image analysis with respect to the ultrasound image U of the current frame.

In step S4, the blood vessel discrimination unit 11 discriminates whether the blood vessels BV1 and BV2 detected in step S3 is the vein or the artery.

In step S5, the blood vessel discrimination unit 11 holds the discrimination result obtained in step S4 in the discrimination result memory 12.

In following step S6, the blood vessel discrimination unit 11 displays the discrimination result held in the discrimination result memory 12 in step S5 while being superimposed on the ultrasound image U of the current frame.

In a case where the processing of step S6 is completed, the process proceeds to step S7, and it is determined whether the operation of the ultrasound diagnostic apparatus 1 ends. In a case where the determination is made that the operation of the ultrasound diagnostic apparatus 1 ends in step S7, the operation of the ultrasound diagnostic apparatus 1 ends. In a case where the determination is made that the operation of the ultrasound diagnostic apparatus 1 does not end in step S7, the process proceeds to step S8.

In step S8, the probe movement amount calculating unit 14 calculates the movement amount of the ultrasound probe 19 in the same manner as in step S1.

In following step S9, the discrimination execution deciding unit 15 determines whether the movement amount of the ultrasound probe 19 calculated in step S8 is larger than the first threshold value. In a case where the determination is made that the movement amount of the ultrasound probe 19 is equal to or smaller than the first threshold value in step S9, the process proceeds to step S16.

Even in a case where the movement amount of the ultrasound probe 19 is equal to or smaller than the first threshold value, the total movement amount may become large as a result of the movements of the ultrasound probe 19 being accumulated in a predetermined time. In step S16, the discrimination execution deciding unit 15 determines whether a predetermined time has elapsed in a state where the movement amount of the ultrasound probe 19 is equal to or smaller than the first threshold value. For example, 10 seconds can be set as a predetermined time. In a case where the determination is made that a predetermined time has not elapsed in a state where the movement amount of the ultrasound probe 19 is equal to or smaller than the first threshold value in step S16, the process proceeds to step S10.

In step S10, the discrimination execution deciding unit 15 decides that the blood vessel discrimination unit 11 does not newly execute discrimination with respect to the blood vessels BV1 and BV2.

In following step S11, the blood vessel discrimination unit 11 displays the latest discrimination result, that is, the discrimination result held in the discrimination result memory 12 in step S5 while being superimposed on the ultrasound image U instead of newly discriminating the blood vessels BV1 and BV2. In a case where the processing of step S9 is completed, the process returns to step S7, and it is determined whether the operation of the ultrasound diagnostic apparatus 1 ends.

In a case where the determination is made that the operation of the ultrasound diagnostic apparatus 1 does not end in step S7, the process proceeds to step S8, and the movement amount of the ultrasound probe 19 is calculated. In following step S9, the determination is made on whether the movement amount of the ultrasound probe 19 calculated in step S8 is larger than the first threshold value. In a case where the determination is made that the movement amount of the ultrasound probe 19 is equal to or smaller than the first threshold value in step S9, the process proceeds to step S16.

In this way, until the determination is made that the operation of the ultrasound diagnostic apparatus 1 ends in step S7, the determination is made that the movement amount of the ultrasound probe 19 is larger than the first threshold value in step S9, or the determination is made that a predetermined time has elapsed in a state where the movement amount of the ultrasound probe 19 is equal to or smaller than the first threshold value in step S16, the processing items of step S7 to step S9, step S16, step S10, and step S11 are repeated.

In step S9, in a case where the determination is made that the movement amount of the ultrasound probe 19 is larger than the first threshold value, or in a case where by repeating the processing items of step S7 to step S9, step S16, step S10, and step S11, the determination is made that a predetermined time has elapsed in a state where the movement amount of the ultrasound probe 19 is equal to or smaller than the first threshold value in step S16, the process proceeds to step S12. In step S12, the discrimination execution deciding unit 15 decides that the blood vessel discrimination unit 11 newly execute discrimination. In a case where processing of step S12 is completed, the process returns to step S1.

As described above, in the ultrasound diagnostic apparatus 1 according to Embodiment 2, in a case where a predetermined time has elapsed in a state where the movement amount of the ultrasound probe 19 is equal to or smaller than the first threshold value, the discrimination execution deciding unit 15 decides that the blood vessel discrimination unit 11 newly executes discrimination, and thus the accurate discrimination result can be obtained even in a case where the total movement amount is large as a result of the movements of the ultrasound probe 19 being accumulated in a predetermined time. Since the decision is made that the blood vessel discrimination unit 11 newly executes discrimination with the lapse of time, the accurate discrimination result can be obtained even in a case where, for example, the subject moves instead of the ultrasound probe 19.

Embodiment 3

Figure 12:
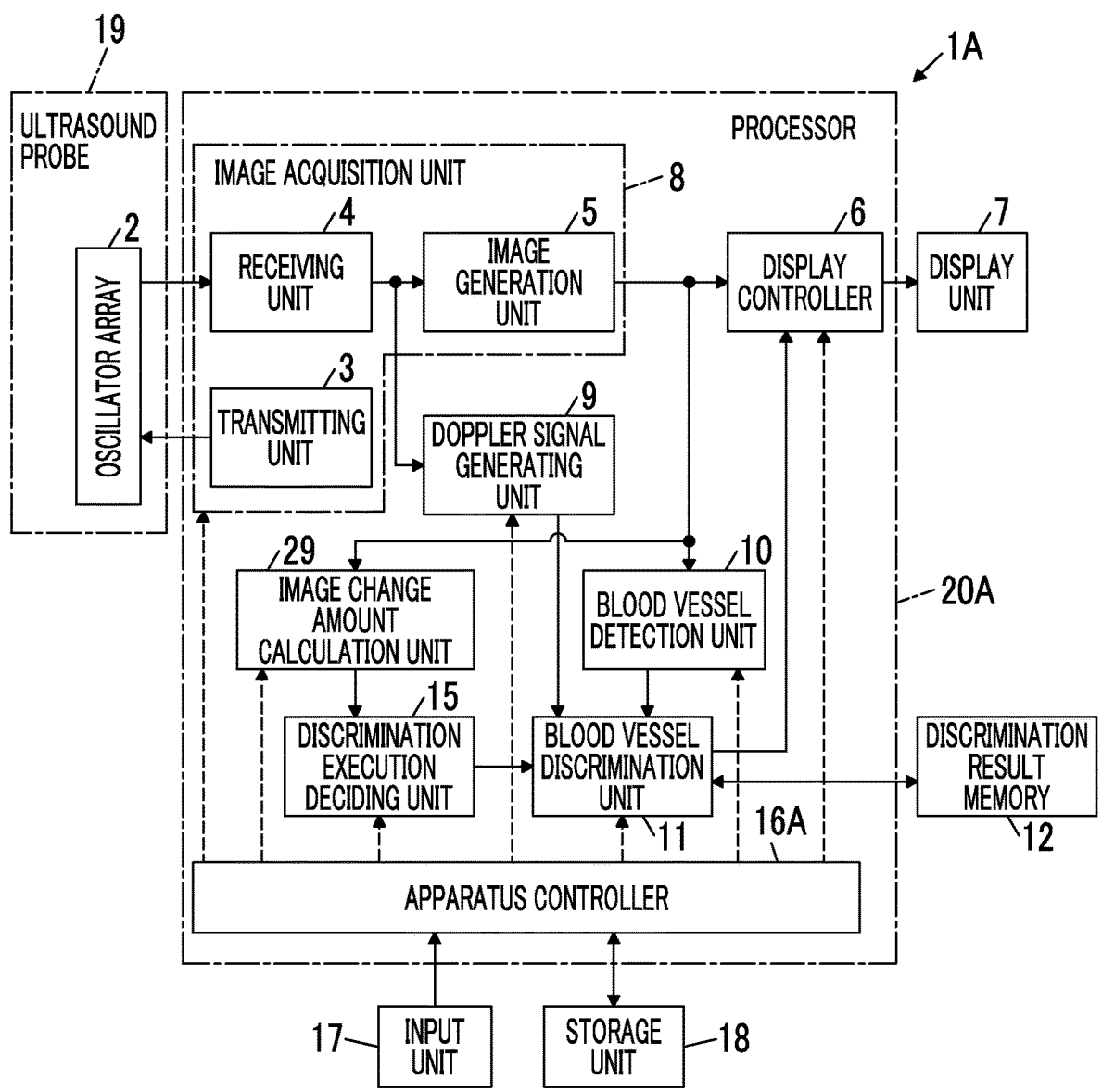
FIG. 12 is a block diagram showing a configuration of an ultrasound diagnostic apparatus according to Embodiment 3 of the present invention.

The configuration of an ultrasound diagnostic apparatus 1A according to Embodiment 3 is shown in FIG. 12. The ultrasound diagnostic apparatus 1A of Embodiment 3 comprises an apparatus controller 16A instead of the apparatus controller 16 in the ultrasound diagnostic apparatus 1 of Embodiment 1 shown in FIG. 1, and further comprises an image change amount calculation unit 29 instead of the motion sensor 13 and the probe movement amount calculating unit 14 which are removed.

As shown in FIG. 12, in the ultrasound diagnostic apparatus 1A, the image change amount calculation unit 29 is connected to the image generation unit 5 of the image acquisition unit 8, and the discrimination execution deciding unit 15 is connected to the image change amount calculation unit 29. The apparatus controller 16A is connected to the display controller 6, the image acquisition unit 8, the Doppler signal generating unit 9, the blood vessel detection unit 10, the blood vessel discrimination unit 11, the discrimination execution deciding unit 15, and the image change amount calculation unit 29. Additionally, the input unit 17 and the storage unit 18 are connected to the apparatus controller 16A. The processor 20A is configured by the display controller 6, the image acquisition unit 8, the Doppler signal generating unit 9, the blood vessel detection unit 10, the blood vessel discrimination unit 11, the discrimination execution deciding unit 15, the apparatus controller 16A, and the image change amount calculation unit 29.

The image change amount calculation unit 29 of the processor 20A calculates the change amount of the ultrasound image between the frames adjacent to each other in time series by performing image analysis with respect to the ultrasound image U acquired by the image acquisition unit 8. The image change amount calculation unit 29 can calculate a movement distance, a rotational angle, or the like of the ultrasound image between the frames adjacent to each other in time series as the change amount of the ultrasound image. The image change amount calculation unit 29 can calculate the change amount of the ultrasound image between the frames adjacent in time series by performing matching between the frames adjacent to each other in time series, and a so-called optical flow method.

The discrimination execution deciding unit 15 of the processor 20A decides whether the blood vessel discrimination unit 11 newly discriminates the blood vessel based on the change amount of the ultrasound image calculated by the image change amount calculation unit 29. For example, the discrimination execution deciding unit 15 can decide that the blood vessel discrimination unit 11 newly discriminates the blood vessel in a case where the change amount of the ultrasound image calculated by the image change amount calculation unit 29 is larger than a predetermined fourth threshold value, and can decide that the blood vessel discrimination unit 11 does not newly discriminate the blood vessel in a case where the change amount of the ultrasound image is equal to or smaller than the fourth threshold value.

Figure 13:
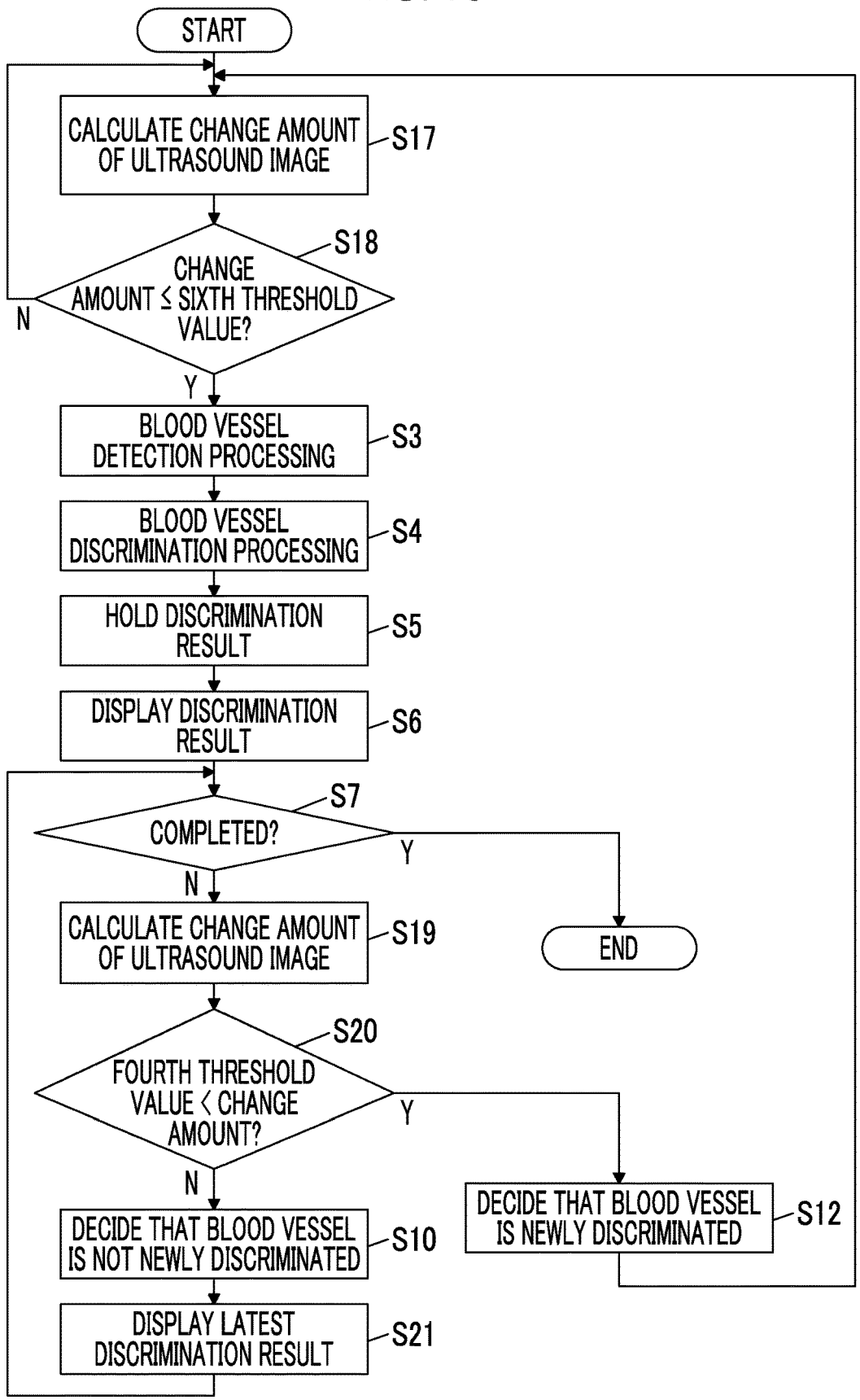
FIG. 13 is a flowchart showing an operation of the ultrasound diagnostic apparatus according to Embodiment 3 of the present invention.

Next, the operation of the ultrasound diagnostic apparatus 1A according to Embodiment 3 will be described using the flowchart shown in FIG. 13. In the flowchart of FIG. 13, step S17, step S18, step S19, step S20, and step S21 are provided instead of step S1, step S2, step S8, step S9, and step S11 of the flowchart shown in FIG. 7, respectively.

In step S17, the image change amount calculation unit 29 calculates the change amount of the ultrasound image between the frames adjacent to each other in time series by performing image analysis with respect to the ultrasound image generated by the image generation unit 5.

In following step S18, the blood vessel detection unit 10 determines whether the ultrasound image between the frames adjacent to each other in time series is substantially unchanged, that is, whether the change amount of the ultrasound image calculated in step S17 is equal to or smaller than the sixth threshold value that is smaller than the fourth threshold value. In a case where the change amount of the ultrasound image is larger than the sixth threshold value, the process returns to step S17, and the change amount of the ultrasound image is newly calculated. In this way, the processing items of step S17 to step S18 are repeated until the determination is made that the change amount of the ultrasound image is equal to or smaller than the sixth threshold value in step S18. In a case where the determination is made that the change amount of the ultrasound image calculated in step S17 is equal to or smaller than the sixth threshold value in step S18, the process proceeds to step S3.

In step S3, the blood vessel detection unit 10 can detect the blood vessels BV1 and BV2 included in the ultrasound image U as shown in FIG. 5 by performing image analysis with respect to the ultrasound image of the current frame acquired by the image acquisition unit 8.

In step S4, the blood vessel discrimination unit 11 discriminates whether the blood vessels BV1 and BV2 detected in step S3 is the vein or the artery.

In step S5, the blood vessel discrimination unit 11 holds the discrimination result obtained in step S4 in the discrimination result memory 12.

In following step S6, the blood vessel discrimination unit 11 displays the discrimination result held in the discrimination result memory 12 in step S5 while being superimposed on the ultrasound image U of the current frame.

In a case where the processing of step S6 is completed, the process proceeds to step S7, and it is determined whether the operation of the ultrasound diagnostic apparatus 1A ends. In step S7, in a case where the determination is made that the operation of the ultrasound diagnostic apparatus 1A ends, the operation of the ultrasound diagnostic apparatus 1A ends. In a case where the determination is made that the operation of the ultrasound diagnostic apparatus 1A does not end in step S7, the process proceeds to step S19.

In step S19, the image change amount calculation unit 29 calculates the change amount of the ultrasound image U between the frames adjacent to each other in time series in the same manner of step S17.

In following step S20, the discrimination execution deciding unit 15 determines whether the change amount of the ultrasound image U calculated in step S19 is larger than the fourth threshold value. In a case where the determination is made that the change amount of the ultrasound image U is equal to or smaller than the fourth threshold value in step S20, the process proceeds to step S10.

In step S10, the discrimination execution deciding unit 15 decides that the blood vessel discrimination unit 11 does not newly execute discrimination with respect to the blood vessels BV1 and BV2.

Figure 14:
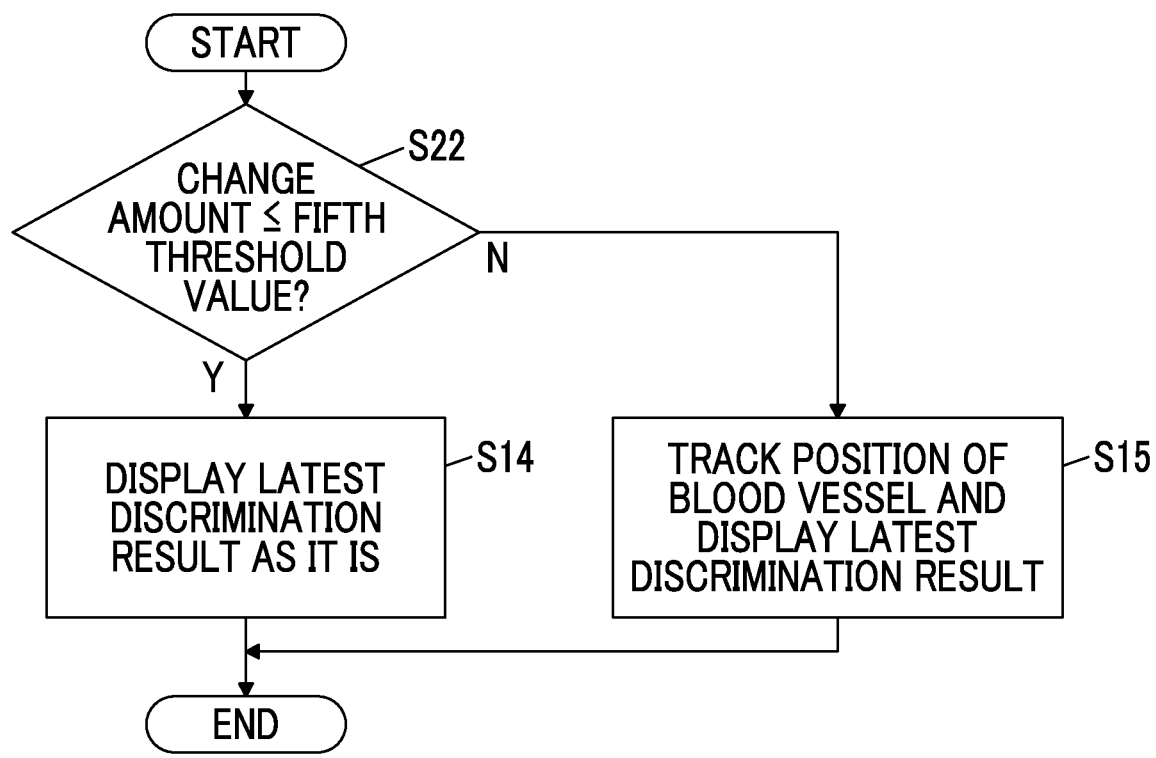
FIG. 14 is a flowchart showing an operation of displaying the latest discrimination result in Embodiment 3 of the present invention.

In following step S21, the blood vessel discrimination unit 11 displays the latest discrimination result, that is, the discrimination result held in the discrimination result memory 12 in step S5 on the display unit 7. Step S21 is processing executed in a case where the determination is made that the change amount of the ultrasound image U is equal to or smaller than the fourth threshold value in step S20, and includes three steps of step S22, step S14, and step S15 as shown in the flowchart of FIG. 14. In the flowchart shown in FIG. 14, step S22 is added instead of step S13 of the flowchart shown in FIG. 8.

First, in step S22, the blood vessel discrimination unit 11 determines whether the change amount of the ultrasound image U calculated in step S19 is equal to or smaller than a predetermined fifth threshold value. The fifth threshold value is a value smaller than the fourth threshold value and equal to or larger than the sixth threshold value. In a case where the determination is made that the change amount of the ultrasound image U is equal to or smaller than the fifth threshold value in step S22, the process proceeds to step S14.

In step S14, the blood vessel discrimination unit 11 determines that the ultrasound image U is not substantially changed, and in step S5, the discrimination result held in the discrimination result memory 12 is maintained. Further, the blood vessel discrimination unit 11 displays the discrimination results for the blood vessels corresponding to the blood vessels BV1 and BV2 shown in FIGS. 5 and 6 held in the discrimination result memory 12 in step S5 while being superimposed on the ultrasound image of the current frame. In a case where processing of step S14 is completed, the processing of step S21 ends.

Also, in a case where the determination is made that the change amount of the ultrasound image U is larger than the fifth threshold value in step S22, the process proceeds to step S15.

In step S15, the blood vessel discrimination unit 11 determines that the ultrasound image U changes, but the change is not so large as to newly perform discrimination processing, tracks the blood vessels BV1 and BV2 included in the ultrasound image U, and maintains the discrimination result held in the discrimination result memory 12 in step S5.

Further, the blood vessel discrimination unit 11 performs processing of displaying the discrimination results for the blood vessels corresponding to the blood vessels BV1 and BV2 included in the ultrasound image U held in the discrimination result memory 12. In this way, in a case where processing of step S15 is completed, the processing of step S21 ends.

In a case where the processing of step S21 ends, the process returns to step S7, and it is determined whether the operation of the ultrasound diagnostic apparatus 1A ends. In a case where the determination is made that the operation of the ultrasound diagnostic apparatus 1A does not end in step S7, the process proceeds to step S19.

In step S19, the image change amount calculation unit 29 calculates the change amount of the ultrasound image U between the frames adjacent to each other in time series.

In following step S20, the determination is made on whether the change amount of the ultrasound image U calculated in preceding step S19 is larger than the fourth threshold value. As described above, until the determination is made on whether the operation of the ultrasound diagnostic apparatus 1A ends in step S7, or the determination is made that the change amount of the ultrasound image U calculated in step S19 is larger than the fourth threshold value in step S20, the processing items of step S7, step S19, step S20, step S10, and step S21 are repeated.

In a case where the determination is made that the change amount of the ultrasound image U calculated in step S19 is larger than the fourth threshold value in step S20, the process proceeds to step S12. In step S12, the discrimination execution deciding unit 15 decides that the blood vessel discrimination unit 11 newly executes discrimination with respect to the blood vessels BV1 and BV2. In this way, in a case where processing of step S12 is completed, the process returns to step S17.

In step S17, the image change amount calculation unit 29 calculates the change amount of the ultrasound image U between the frames adjacent to each other in time series.

In following step S18, the blood vessel detection unit 10 determines whether the change amount of the ultrasound image U calculated in step S17 is equal to or smaller than the sixth threshold value. In step S18, in a case where the determination is made that the change amount of the ultrasound image U is larger than the sixth threshold value, the process returns to step S17, and in a case where the determination is made that the change amount of the ultrasound image U is equal to or smaller than the sixth threshold value, the process proceeds to step S3.

In step S3, the blood vessel detection unit 10 performs processing of detecting the blood vessels BV1 and BV2 included in the ultrasound image U is performed by performing image analysis with respect to the ultrasound image U of the current frame.

In step S4, the blood vessel discrimination unit 11 performs processing of discriminating whether the blood vessels BV1 and BV2 detected in step S3 is the vein or the artery.

In step S5, the blood vessel discrimination unit 11 updates the discrimination result held in the discrimination result memory 12 using the discrimination result newly obtained in step S4.

In step S6, the blood vessel discrimination unit 11 displays the discrimination result updated in step S5 on the display unit 7 while being superimposed on the ultrasound image U of the current frame.

In the following step S7, it is determined whether the operation of the ultrasound diagnostic apparatus 1A ends. In step S7, in a case where the determination is made that the operation of the ultrasound diagnostic apparatus 1A does not end, the process proceeds to step S19, and in a case where the determination is made than the operation of the ultrasound diagnostic apparatus 1A ends, the operation of the ultrasound diagnostic apparatus 1A ends.

As described above, in the ultrasound diagnostic apparatus 1A according to Embodiment 3, even in a case where decision is made on whether the blood vessel discrimination unit 11 newly discriminates the blood vessels BV1 and BV2 in the ultrasound image U based on the change amount of the ultrasound images U adjacent to each other in time series, it is possible to reduce the power consumption in the ultrasound diagnostic apparatus 1A while discriminating the blood vessels BV1 and BV2 by not performing unnecessary discrimination of the blood vessels BV1 and BV2 in a case where the change amount of the ultrasound image U is equal to or smaller than the fourth threshold value, in the same manner of aspects of Embodiments 1 and 2.

In Embodiment 3, similar to Embodiment 2, even in a case where a state in which the change amount of the ultrasound image U is equal to or smaller than the fourth threshold value continues for a predetermined time, the discrimination execution deciding unit 15 can decide that the blood vessel discrimination unit 11 newly executes discrimination. That is, in step S20 of FIG. 13, even in a case where the change amount of the ultrasound image U is equal to or smaller than the fourth threshold value, in a case where a predetermined time has elapsed in a state where the change amount of the ultrasound image U is equal to or smaller than the fourth threshold value, the process proceeds to step S12. In step S12, the discrimination execution deciding unit 15 decides that the blood vessel discrimination unit 11 newly execute discrimination. In a case where processing of step S12 is completed, the process returns to step S1.

Accordingly, with the ultrasound diagnostic apparatus 1A, in a case where a predetermined time has elapsed in a state where the change amount of the ultrasound image U is equal to or smaller than the fourth threshold value, the discrimination execution deciding unit 15 decides that the blood vessel discrimination unit 11 newly executes discrimination, and thus the accurate discrimination result can be obtained even in a case where the total movement amount is large as a result of the change of the ultrasound image U being accumulated in a predetermined time. Since the decision is made that the blood vessel discrimination unit 11 newly executes discrimination with the lapse of time, the accurate discrimination result can be obtained even in a case where, for example, the subject moves instead of the ultrasound probe 19.

From the above description, the ultrasound diagnostic apparatus according to the following supplementary notes 1 to 18 can be grasped.

Supplementary Note 1

An ultrasound diagnostic apparatus comprising an ultrasound probe, and a processor, wherein the processor is configured to acquire an ultrasound image sequentially by transmitting an ultrasound beam toward a subject from an ultrasound probe, detect a blood vessel included in the acquired ultrasound image, discriminate whether the detected blood vessel is a vein or an artery, and decide whether discrimination is newly executed with respect to the ultrasound image of a current frame based on a movement amount of the ultrasound probe or a change amount of the ultrasound image between frames.

Supplementary Note 2

The ultrasound diagnostic apparatus according to supplementary note 1 further comprising a motion sensor that is attached to the ultrasound probe, wherein the processor is further configured to calculate the movement amount of the ultrasound probe based on a value measured by the motion sensor, decide whether discrimination is executed based on the calculated movement amount of the ultrasound probe.

Supplementary Note 3

The ultrasound diagnostic apparatus according to supplementary note 2 further comprising a discrimination result memory that holds a latest discrimination result, wherein the processor is further configured to, in a case where the calculated movement amount of the ultrasound probe is equal to or smaller than a predetermined first threshold value, decide that discrimination is not newly executed with respect to the ultrasound image of the current frame, and maintain the latest discrimination result held in the discrimination result memory.

Supplementary Note 4

The ultrasound diagnostic apparatus according to supplementary note 3, wherein the processor is further configured to, in a case where the calculated movement amount of the ultrasound probe is equal to or smaller than the first threshold value and larger than a second threshold value that is smaller than the first threshold value, track a position of the blood vessel in the ultrasound image from the frame in which the latest discrimination is executed to the current frame, and maintain the latest discrimination result held in the discrimination result memory.

Supplementary Note 5

The ultrasound diagnostic apparatus according to supplementary note 3 or 4, wherein the processor is further configured to, in a case where the calculated movement amount of the ultrasound probe is larger than the first threshold value, decide that discrimination is newly executed with respect to the ultrasound image of the current frame, and discriminate whether the blood vessel in the ultrasound image of the current frame is a vein or an artery, and update the latest discrimination result held in the discrimination result memory based on the discrimination result.

Supplementary Note 6

The ultrasound diagnostic apparatus according to supplementary note 3 or 4, wherein the processor is further configured to, in a case where a state in which the calculated movement amount of the ultrasound probe is equal to or smaller than the first threshold value continues for a predetermined time, decide that discrimination is newly executed with respect to the ultrasound image of the current frame, and discriminate whether the blood vessel in the ultrasound image of the current frame is a vein or an artery, and update the latest discrimination result held in the discrimination result memory based on the discrimination result.

Supplementary Note 7

The ultrasound diagnostic apparatus according to supplementary note 5 or 6, wherein the processor is further configured to newly execute discrimination on whether the blood vessel in the ultrasound image of the current frame is a vein or an artery after the calculated movement amount of the ultrasound probe becomes equal to or smaller than a third threshold value that is smaller than the first threshold value.

Supplementary Note 8

The ultrasound diagnostic apparatus according to any one of supplementary notes 3 to 7, further comprising a display device that displays the acquired ultrasound image and the discrimination result held in the discrimination result memory.

Supplementary Note 9

The ultrasound diagnostic apparatus according to any one of supplementary notes 2 to 8, wherein the calculated movement amount of the ultrasound probe includes at least one of a moving speed of the ultrasound probe in parallel movement, a change amount in a movement direction of the ultrasound probe, or an angular velocity of the ultrasound probe in rotational movement.

Supplementary Note 10

The ultrasound diagnostic apparatus according to any one of supplementary notes 2 to 9, wherein the motion sensor consists of at least one of an acceleration sensor, a gyro sensor, a magnetic sensor, or a position sensor of a global positioning system.

Supplementary Note 11

The ultrasound diagnostic apparatus according to supplementary note 1, wherein the processor is further configured to calculate the change amount of the ultrasound image between the frames by performing image analysis with respect to the acquired ultrasound image, and decide whether discrimination is executed based on the calculated change amount of the ultrasound image.

Supplementary Note 12

The ultrasound diagnostic apparatus according to supplementary note 11 further comprising a discrimination result memory that holds a latest discrimination result, wherein the processor is further configured to, in a case where the calculated change amount of the ultrasound image between the frames is equal to or smaller than a predetermined fourth threshold value, decide that discrimination is not newly executed with respect to the ultrasound image of the current frame, and maintain the latest discrimination result held in the discrimination result memory.

Supplementary Note 13

The ultrasound diagnostic apparatus according to supplementary note 12, wherein the processor is further configured to, in a case where the acquired change amount of the ultrasound image between the frames is equal to or smaller than the fourth threshold value and larger than a fifth threshold value that is smaller than the fourth threshold value, track a position of the blood vessel in the ultrasound image from the frame in which latest discrimination is executed to the current frame, and maintain the latest discrimination result held in the discrimination result memory.

Supplementary Note 14

The ultrasound diagnostic apparatus according to supplementary note 12 or 13, wherein the processor is further configured to, in a case where the calculated change amount of the ultrasound image between the frames is larger than the fourth threshold value, decide that discrimination is newly executed with respect to the ultrasound image of the current frame, and discriminate whether the blood vessel in the ultrasound image of the current frame is a vein or an artery, and update the latest discrimination result held in the discrimination result memory based on the discrimination result.

Supplementary Note 15

The ultrasound diagnostic apparatus according to supplementary note 12 or 13, wherein the processor is further configured to, in a case where a state in which the calculated change amount of the ultrasound image between the frames is smaller than the fourth threshold value continues for a predetermined time, decide that discrimination is newly executed with respect to the ultrasound image of the current frame, and discriminate whether the blood vessel in the ultrasound image of the current frame is a vein or an artery, and update the latest discrimination result held in the discrimination result memory based on the discrimination result.

Supplementary Note 16

The ultrasound diagnostic apparatus according to supplementary note 14 or 15, wherein the processor is further configured to newly execute discrimination on whether the blood vessel in the ultrasound image of the current frame is a vein or an artery after the calculated change amount of the ultrasound image between the frames becomes equal to or smaller than a sixth threshold value that is smaller than the fourth threshold value.

Supplementary Note 17

The ultrasound diagnostic apparatus according to any one of supplementary notes 12 to 16, further comprising a display device that displays the acquired ultrasound image and the discrimination result held in the discrimination result memory.

Supplementary Note 18

The ultrasound diagnostic apparatus according to any one of supplementary notes 1 to 17, further comprising a receiving circuit that receives an ultrasound echo in the subject by the ultrasound probe and generates a received signal, wherein the processor is further configured to generate a Doppler signal based on the received signal generated by the receiving circuit, and discriminate whether the blood vessel is a vein or an artery based on the generated Doppler signal.

EXPLANATION OF REFERENCES

1, 1A: ultrasound diagnostic apparatus
2: oscillator array

3: transmitting unit
4: receiving unit
5: image generation unit
6: display controller
7: display unit
8: image acquisition unit
9: Doppler signal generating unit
10: blood vessel detection unit
11: blood vessel discrimination unit
12: discrimination result memory
13: motion sensor
14: probe movement amount calculating unit
15: discrimination execution deciding unit
16, 16A: apparatus controller
17: input unit
18: storage unit
19: ultrasound probe
20, 20A: processor
21: amplification unit
22: AD conversion unit
23: signal processing unit
24: DSC
25: image processing unit
26: orthogonal detection unit
27: high-pass filter
28: fast Fourier transformer
29: image change amount calculation unit
BV1, BV2, BV3, BV4: blood vessel
E1, E2: surrounding line
T1, T2: text
U: ultrasound image

What is claimed is:

1. An ultrasound diagnostic apparatus comprising:
an ultrasound probe attached to a motion sensor;
a processor; and
a discrimination result memory,
wherein the processor is configured to:
sequentially calculate movement amounts of the ultrasound probe based on values measured by the motion sensor,
sequentially acquire ultrasound images by transmitting ultrasound beams toward a subject from the ultrasound probe,
sequentially detect a blood vessel from the sequentially acquired ultrasound images,
upon keeping calculating the movement amounts that are equal to or smaller than a first predetermined threshold value during a constant time span,
execute a discrimination process of determining whether the detected blood vessel is a vein or an artery, and
store a result of the discrimination process in the discrimination result memory.

2. The ultrasound diagnostic apparatus according to claim 1,
wherein the processor is further configured to:
upon calculating the movement amounts that are equal to or smaller than the first predetermined threshold value and larger than a second predetermined threshold value, where the second predetermined threshold value is smaller than the predetermined first threshold value,
track a position of the blood vessel in the sequentially acquired ultrasound images from the frame in which a latest discrimination is executed to a current frame, and
maintain the result of the discrimination process stored in the discrimination result memory.

3. The ultrasound diagnostic apparatus according to claim 1,
wherein the processor is further configured to:
update discrimination on whether the blood vessel in the ultrasound image of the current frame is a vein or an artery after the calculated movement amount of the ultrasound probe becomes equal to or smaller than a second threshold value that is smaller than the first threshold value.

4. The ultrasound diagnostic apparatus according to claim 1, further comprising:
a display device configured to display the sequentially acquired ultrasound images and the result of the discrimination process stored in the discrimination result memory.

5. The ultrasound diagnostic apparatus according to claim 1,
wherein the calculated movement amounts of the ultrasound probe includes at least one of a moving speed of the ultrasound probe in parallel movement, a change amount in a movement direction of the ultrasound probe, or an angular velocity of the ultrasound probe in rotational movement.

6. The ultrasound diagnostic apparatus according to claim 1,
wherein the motion sensor consists of at least one of an acceleration sensor, a gyro sensor, a magnetic sensor, or a position sensor of a global positioning system.

7. An ultrasound diagnostic apparatus comprising:
an ultrasound probe;
a processor; and
a discrimination result memory,
wherein the processor is configured to:
sequentially acquire ultrasound images by transmitting ultrasound beams toward a subject from the ultrasound probe,
sequentially calculate change amounts of the sequentially acquired ultrasound images between frames by performing image analysis with respect to the sequentially acquired ultrasound images,
sequentially detect a blood vessel from the sequentially acquired ultrasound images,
upon keeping calculating the change amounts that are equal to or smaller than a first predetermined threshold value during a constant time span,
execute a discrimination process of determining whether the detected blood vessel is a vein or an artery, and
store a result of the discrimination process in the discrimination result memory.

8. The ultrasound diagnostic apparatus according to claim 7,
wherein the processor is further configured to:
update discrimination on whether the blood vessel in the ultrasound image of the current frame is a vein or an artery after the calculated change amount of the ultrasound image between the frames becomes equal to or smaller than a second threshold value that is smaller than the first predetermined threshold value.

9. The ultrasound diagnostic apparatus according to claim 1, further comprising:
a receiving circuit configured to receive an ultrasound echo in the subject by the ultrasound probe and generate a received signal, wherein the processor is further configured to generate a Doppler signal based on the received signal generated by the receiving circuit, and discriminate whether the blood vessel is a vein or an artery based on the generated Doppler signal.

10. A method of controlling an ultrasound diagnostic apparatus, the method comprising:
sequentially calculating movement amounts of an ultrasound probe to which a motion sensor is attached based on values measured by the motion sensor;
sequentially acquiring ultrasound images by transmitting ultrasound beams toward a subject from the ultrasound probe;
sequentially detecting a blood vessel from the sequentially acquired ultrasound images;
upon keeping calculating the movement amounts that are equal to or smaller than a first predetermined threshold value during a constant time span,
executing a discrimination process of determining whether the detected blood vessel is a vein or an artery; and
storing a result of the discrimination process in a discrimination result memory.

11. The ultrasound diagnostic apparatus according to claim 7,
wherein the processor is further configured to:
upon calculating the change amounts that are equal to or smaller than the first predetermined threshold value and larger than a second predetermined threshold value, where the second predetermined threshold value is larger than the first predetermined threshold value,
track a position of the blood vessel in the sequentially acquired ultrasound images from the frame in which a latest discrimination is executed to a current frame, and
maintain the result of the discrimination process stored-held in the discrimination result memory.

12. The ultrasound diagnostic apparatus according to claim 7, further comprising:
a display device configured to display the sequentially acquired ultrasound images and the result of the discrimination process stored in the discrimination result memory.

13. The ultrasound diagnostic apparatus according to claim 7, further comprising:
a receiving circuit configured to receive an ultrasound echo in the subject by the ultrasound probe and generate a received signal,
wherein the processor is further configured to generate a Doppler signal based on the received signal generated by the receiving circuit, and discriminate whether the blood vessel is a vein or an artery based on the generated Doppler signal.

14. A method of controlling an ultrasound diagnostic apparatus, the method comprising:
sequentially acquiring ultrasound images by transmitting ultrasound beams toward a subject from an ultrasound probe being attached a motion sensor;
sequentially calculating change amounts of the sequentially acquired ultrasound images between frames by performing image analysis with respect to the sequentially acquired ultrasound images;
sequentially detecting a blood vessel from the sequentially acquired ultrasound images;
upon keeping calculating the change amounts that are equal to or smaller than a first predetermined threshold value during a constant time span,
executing a discrimination process of determining whether the detected blood vessel is a vein or an artery; and
storing a result of the discrimination process in a discrimination result memory.

* * * * *